US008372040B2

(12) United States Patent
Huang et al.

(10) Patent No.: US 8,372,040 B2
(45) Date of Patent: Feb. 12, 2013

(54) PORTABLE DRUG DELIVERY DEVICE INCLUDING A DETACHABLE AND REPLACEABLE ADMINISTRATION OR DOSING ELEMENT

(75) Inventors: Joseph Zhili Huang, Plainsboro, NJ (US); Guy DiPierro, Hamilton, NJ (US)

(73) Assignee: Chrono Therapeutics, Inc., Cambridge, MA (US)

( * ) Notice: Subject to any disclaimer, the term of this patent is extended or adjusted under 35 U.S.C. 154(b) by 1842 days.

(21) Appl. No.: 11/440,169

(22) Filed: May 24, 2006

(65) Prior Publication Data
US 2006/0271020 A1 Nov. 30, 2006

Related U.S. Application Data

(60) Provisional application No. 60/594,981, filed on May 24, 2005, provisional application No. 60/720,076, filed on Sep. 24, 2005.

(51) Int. Cl.
*A61M 1/00* (2006.01)
*A61K 9/22* (2006.01)
(52) U.S. Cl. ..................... 604/151; 604/890.1
(58) Field of Classification Search ............ 604/890.1, 604/892.1, 65–68
See application file for complete search history.

(56) References Cited

U.S. PATENT DOCUMENTS

| 5,097,834 | A | * | 3/1992 | Skrabal | 600/366 |
|---|---|---|---|---|---|
| 5,352,456 | A | | 10/1994 | Fallon et al. | |
| 5,370,635 | A | | 12/1994 | Strausak et al. | |
| 5,820,875 | A | | 10/1998 | Fallon et al. | |
| 6,068,853 | A | | 5/2000 | Giannos et al. | |
| 6,214,379 | B1 | | 4/2001 | Hermelin | |
| 6,436,078 | B1 | * | 8/2002 | Svedman | 604/313 |
| 6,638,528 | B1 | | 10/2003 | Kanios | |
| 6,723,086 | B2 | | 4/2004 | Bussek et al. | |
| 6,861,066 | B2 | | 3/2005 | Van de Casteele | |
| 6,867,342 | B2 | | 3/2005 | Johnston et al. | |
| 6,887,202 | B2 | | 5/2005 | Currie et al. | |
| 7,780,981 | B2 | | 8/2010 | DiPierro et al. | |
| 2002/0169439 | A1 | * | 11/2002 | Flaherty | 604/891.1 |
| 2003/0065294 | A1 | * | 4/2003 | Pickup et al. | 604/304 |
| 2003/0065924 | A1 | * | 4/2003 | Wuidart et al. | 713/176 |
| 2005/0034842 | A1 | | 2/2005 | Huber et al. | |
| 2005/0182307 | A1 | | 8/2005 | Currie et al. | |
| 2005/0238704 | A1 | | 10/2005 | Zumbrunn et al. | |

OTHER PUBLICATIONS

Lamberg, "Chronotherapeutics: Implications for Drug Therapy," *American Pharmacy*, vol. NS31 (11): pp. 20-23 (1991).

* cited by examiner

*Primary Examiner* — Nicholas Lucchesi
*Assistant Examiner* — Jenna Zhang
(74) *Attorney, Agent, or Firm* — Foley & Lardner LLP

(57) ABSTRACT

A device for transdermal drug delivery and administration of differing dosages at specific times of the day automatically pursuant to a pre-programmed dosage profile. The device includes a control and display unit, a two-part dispensing mechanism, a drug reservoir, an administration element, and a solvent removal element. The dispensing mechanism may be a peristaltic pump having an active portion with a motor, a roller, a mounting plate and a detachable passive portion with tubing and a housing. The motor and roller are mounted in the reusable portion of the delivery device with the control unit and a power source. The speed of the micromotor is controlled by the control unit, so that the turning speed of the roller is controlled which, in turn, controls the flow rate to the administration. The passive portion and drug reservoir are detachable along with the administration element for attaching a new dosing reservoir.

10 Claims, 20 Drawing Sheets

PORTABLE DRUG DELIVERY DEVICE INCLUDING A DETACHABLE AND REPLACEABLE ADMINISTRATION OR DOSING ELEMENT

CROSS-REFERENCE TO RELATED APPLICATIONS

This application claims the benefit of U.S. Provisional Application No. 60/594,981 filed May 24, 2005 and U.S. Provisional Application No. 60/720,076 filed Sep. 24, 2005, both of which are incorporated herein by reference in their entirety.

BACKGROUND OF THE INVENTION

1. Field of the Invention

The present invention relates to a device for controllable dispensing of active substance, such as a chemical substance, a medication, a drug, or the like, to a person or other mammal, and more particularly, the invention is related to a portable device usable for transdermal and subcutaneous drug delivery or compound delivery in a programmable, automated, and/or controllable manner including control of the dose and timing of delivery to the patient. The invention further relates to the controllable stopping of compound delivery to the body. The invention further relates to the field of chronobiology in that the invention systems can be designed to modulate active agent delivery in accordance with biological rhythms pursuant to automated and/or pre-programmed dosage profiles. Bioactive substances are delivered transdermally into a body in a manner that is synchronized with biological processes and/or biological rhythms, and/or narcotic or other addiction cycles or other intra body or externally desired cycles so as to improve performance of the substance in the body or otherwise achieve a desired result by controlling blood plasma concentrations of a compound. The invention also relates to overcoming active agent tolerance, which may be experienced from continuous administration, overcoming active agent skin irritation, which may be experienced from continuous administration by allowing skin rest periods, improve patient compliance, and in some cases reducing the amount of drug needed per dose due to advantages of biosynchronization or programmed dosing. A programmable heating element may also be utilized to automatically heat the skin at precise times or intervals to assist in permeation and/or aid in the stopping of dosing.

2. Relevant Background

Medications provide effective treatments for a variety of illnesses. It is often preferred that medication is applied at a certain time or with a certain time pattern and in a manner that keeps the concentration of medication at a certain value to achieve a desired therapeutic result most efficiently. There are some medications that are only able to release effective pharmaceutical substances over a long period of time. Further, there are effective substances that are partially or totally inactivated following oral ingestion by the highly acidic environment of the stomach or by the filter impact of the liver. In order to overcome such problems, drugs are administered by either by transdermal delivery through the skin (e.g., with a patch) or subcutaneously with a needle or continuously by drip, with these later two methods being common parenteral methods for drug delivery. For a long-term treatment, the parenteral methods may be uncomfortable for the patient because of the repeated injury by needle injections and the limited liberty of action due to intravenous drip apparatus.

Patches are a form of transdermal drug delivery that is applied on the surface of the skin. These patches are capturing more and more attention in recent years because they are portable, comfortable, and suitable for patients with drug delivery in continuous dosages over a relatively long period of time without requiring active participation of the patient.

In the last decade, portable dispensing systems have been developed to provide a more flexible, precise and complex administration of drugs. Generally, the dispensing systems comprise a reservoir for a drug, a dispensing unit, and a patch (or a membrane that is permeable to the active substance, drug, or the like but relatively impermeable to a solvent in which the active substance is mixed in the reservoir). The reservoir through the dispensing unit is interconnected to the patch. The dispensing unit controls the releasing of the drug in the reservoir to the patch. The efficiency for patch transdermal drug delivery depends mainly on the diffusion rate of the effective substances through the skin. Maintenance of the concentration of the effective substances on the patch is essential to achieve the desirable diffusion rate. However, it has proven problematic to effectively control the concentration of substances on the patch in an effective manner. Further, it has proven difficult to provide an inexpensive portable device that allows a user or patient to easily refill the reservoir and to otherwise maintain the device.

In the field of drug delivery, it is recognized that supplying the drug in a correct temporal pattern is an important attribute of any drug delivery methodology. Controlled release drug delivery systems are intended to improve the response to a drug and/or lessen side effects of a drug. The recurring interest in chronopharmacology demonstrates the fact that biological rhythms are an important aspect of clinical pharmacology and should be taken into account when evaluating drug delivery systems (Hrushesky, W., J. Cont. Rel. 19:363 (1992), Lemmer, B., Adv. Drug Del. Rev. 6:19 (1991), Youn, C. B. J. Cont. Rel. 98 (3) 337 (2004) and Youn, C. B. J., Ed., "Chronopharmaceutics," John Wiley & Sons, New York.

The onset and symptoms of diseases such as asthma attacks, coronary infarction, angina pectoris, stroke and ventricular tachycardia are circadian phase dependent. In addition, certain addictions (such as cigarette smoking) have times of day based on a persons circadian rhythms when symptoms peak. In humans, variations during the 24 h day in pharmacokinetics (chrono-pharmacokinetics) have been shown for cardiovascular active drugs (propranolol, nifedipine, verapamil, enalapril, isosorbide 5-mononitrate and digoxin), anti-asthmatics (theophylline and terbutaline), anti-cancer drugs, psychotropics, analgesics, local anesthetics and antibiotics, to mention but a few. Even more drugs have been shown to display significant variations in their effects throughout the day (chronopharmacodynamics and chronotoxicology) even after chronic application or constant infusion (Ohdo, S. Drug Safety 26 (14) 999-1010 (2003)). Moreover, there is clear evidence that dose/concentration-response relationships can be significantly modified based on the time of day. Thus, circadian time has to be taken into account as an important variable influencing a drug's pharmacokinetics and its effects or side-effects (Bruguerolle, B., *Clin*. Pharmacokinet. August 35 (2) 83-94 (1998)).

Studies indicate that the onset of certain diseases show strong circadian temporal dependency. This has led to the need for timed patterning of drug delivery as opposed to constant drug release (Lemmer B., Ciba Found Symp. 183: 235-47; discussion 247-53 (1995). The term "controlled release" refers generally to delivery mechanisms that make an active ingredient available to the biological system of a host in a manner that supplies the drug according to a desired temporal pattern. Controlled release drug delivery systems may be implemented using: a) instantaneous release systems; b) delayed release systems, and c) sustained release systems. In most cases, controlled release systems are designed to maintain a sustained plasma level of an active ingredient in a drug within a human or animal host over a period of time.

Instantaneous release refers to systems that make the active ingredient available immediately after administration to the biosystem of the host. Instantaneous release systems include continuous or pulsed intravenous infusion or injections. Such systems provide a great deal of control because administration can be both instantaneously started and stopped and the delivery rate can be controlled with great precision. However, the administration is undesirably invasive as they involve administration via a puncture needle or catheter.

Delayed release refers to systems in which the active ingredient made available to the host at some time after administration. Such systems include oral as well as injectable drugs in which the active ingredient is coated or en-capsulated with a substance that dissolves at a known rate so as to release the active ingredient after the delay. Unfortunately, it is often difficult to control the degradation of the coating or encapsulant after administration and the actual performance will vary from patient to patient.

Sustained Release generally refers to release of active ingredient such that the level of active ingredient available to the host is maintained at some level over a period of time. Like delayed release systems, sustained release systems are difficult to control and exhibit variability from patient to patient. Due to the adsorption through the gastrointestinal tract, drug concentrations rise quickly in the body when taking a pill, but the decrease is dependent on excretion and metabolism, which cannot be controlled. In addition, the adsorption through the gastrointestinal tract in many cases leads to considerable side effects (such as ulcers), and can severely damage the liver.

Transdermal therapeutic systems (TTS) have been developed primarily for sustained release of drugs in situations where oral sustained release systems are inadequate. In some cases, drugs cannot be effectively administered orally because the active ingredients are destroyed or altered by the gastrointestinal system. In other cases the drug may be physically or chemically incompatible with the coatings and/or chelating agents used to implement sustained release. In other cases a transdermal delivery system may provide sustained release over a period of days or weeks whereas orally administered drugs may offer sustained performance over only a few hours. A wide variety of active substances can be delivered through transdermal systems so long as the active substance can be provided in a form that can cross the skin barrier, see for example, U.S. Pat. No. 6,638,528, which is incorporated herein by reference.

In most cases transdermal delivery systems are passive, taking the form of a patch that is attached to the skin by an adhesive. The TTS includes a quantity of the active substance, along with a suitable carrier if need be, in a reservoir, matrix or in the adhesive itself. Once applied, the active ingredient diffuses through the skin at a rate determined by the concentration of the active substance and the diffusivity of the active substance. However, a variety of physical and chemical processes at the skin/patch boundary affect the delivery rate and may eventually inhibit drug delivery altogether.

The original performance target for controlled drug delivery is to achieve a zero-order release rate of the drug, so that a constant efficacious drug concentration is maintained in the blood plasma. However, more than two decades of research in chronobiology and chronopharmacology have demonstrated the importance of biological rhythms to the dosing of medications as well as determine the influence of a patient's circadian or other biological rhythms on drug efficacy and efficiency. This research reveals that certain disease symptoms follow a daily pattern, with peak symptoms at certain times of the day. It has been widely acknowledged that hormones, neurotransmitters and other intra-body compounds are released in different amounts at different times of the day pursuant to daily patterns.

The new approach stems from a growing body of research that demonstrates that certain diseases tend to get worse at certain times of the day. Also, certain disease symptoms have peak periods when cravings are at their highest. By synchronizing medications with a patient's body clock, and/or addiction cycles, many physicians believe that the drugs will work more effectively and with fewer side effects. In some cases, the improvements have been so pronounced that doctors have been able to reduce dosages. Circadian physiologic processes have been found to alter drug absorption, distribution, metabolism, and excretion. As a result, drug doses need to be adjusted to meet the differing needs of target organs or tissues at various times of the day (see, L. Lamberg, American Pharmacy, N831 (11): 20-23 (1991)).

The continued interest in chronopharmacology shows the ever-increasing need to develop technologies to control the temporal profile in drug delivery. Research findings suggest that the onset and severity of many diseases are cyclic in nature, or follow circadian patterns. Addiction symptoms also show cyclical nature. For example, cigarette smokers experience peak nicotine cravings upon waking, but nicotine is a stimulant, so there is a clear advantage to have an automated drug delivery system that can be programmed to not release nicotine during the sleep cycle, but to release nicotine prior to waking, because this would effectively combat peak morning nicotine cravings while removing the adverse side effect of sleep cycle nicotine disturbances. Drug tolerance adds to the need for modulation of drug dosing profiles. Additionally, skin irritation and sensitization caused by medications may require intervals during which no drug is administered. For example, fentanyl when administered continuously without rest periods can cause severe skin irritation, so there is a clear advantage of allowing the skin a "rest period" when no fentanyl is delivered in order to decrease adverse skin irritation and give the skin a chance to recover. Therefore, this improved form of drug delivery will be very important to people who need medicine easily, painlessly and automatically delivered to their bodies in timed increments (see Smolensk, M. H. & Lamberg, L. *Body Clock Guide to Better Health. How to Use Your Body's Natural Clock to Fight Illness and Achieve Maximum Health*, Henry Holt & Company, New York (2001) and Grimes, J. et al., *J Pharmacol Exp Ther* 285 (2): 457-463 (1998)).

Active transdermal delivery systems have been developed to help regulate the delivery rate by providing mechanisms to improve drug delivery over time by "pumping" the active ingredient. One such system, (U.S. Pat. No. 5,370,635), describes a system for delivering a medicament and dispensing it to an organism for a relatively long period of time, for example at least a few days. The device can be adapted for positioning on the surface of the skin of a human or possibly an animal body in order to apply a medicament thereto from the outer side thereof. Conventional transdermal systems circumvent the disadvantages of the adsorption through the gastrointestinal tract, but they do not optimize or tailor the dosing regiment to offset peak symptoms. In addition the constant transdermal delivery of a drug can lead to severe side effects, including debilitating sleep disorders (if the drug is a stimulant) and ever increasing tolerance (such as pain medications).

A simple type of transdermal chronotherapy is a biphasic profile, in which the drug concentration changes from a high to a low level (or vice versa) over time. Although the system can be physically applied or removed to alter the drug level, patient compliance with this procedure may be difficult, particularly during inconvenient hours. To generate a biphasic profile, the delivery system may utilize an external regulator, as described in Fallon et al. (U.S. Pat. No. 5,352,456) which illustrates a device for drug administration through intact skin that provides an initial pulse in the flux of the drug through the skin followed by a substantially lower flux of drug through the skin. Additionally, Fallon et al. (U.S. Pat. No. 5,820,875) later describe a device for the administration of a drug through an area of intact skin over a period of time in which the flux of the drug through the skin varies temporally in a controlled manner; The device is such that the skin flux of the drug varies in a controlled manner over the period of administration, typically from a high flux in the initial stage of administration to a lower flux in the later stage of administration.

Transdermal temporally controlled drug delivery systems, proposed by Giannos et al. (U.S. Pat. No. 6,068,853) coupled pH oscillators with membrane diffusion in order to generate a periodic release of a drug or active ingredient transdermally, without external power sources and/or electronic controllers. The intent was to address chronotherapy with a pulsatile transdermal system. The strategy was based on the observation that a drug may be rendered charged or uncharged relative to its $pK_a$ value. Since only the uncharged form of a drug can permeate across lipophilic membranes, including the skin, a periodic delivery profile may be obtained by oscillating the pH of the drug solution (see Giannos, S. A., "Pulsatile Delivery of Drugs and Topical Actives," in "Novel Topical Actives and Delivery Systems: Cosmetics, Dermatologicals and Transdermals", Edited by John. J. Wille, Jr.: Blackwell Publishing, Oxford UK (In press)).

Recently, an orally administered drug for arthritis treatment has suggested a chronotherapeutic approach using a delay release system. The delay is scheduled to release the active ingredient at the beginning of an interleukin 6 cascade that is believed to cause early morning stiffness in rheumatoid arthritis patients. By attempting to synchronize the drug delivery with a biological cycle it is believed that low doses may be used to achieve desired results. However, this system does not overcome the limitations of delayed release systems described above.

Although it may possible to meet the requirements of chronopharmacology with pills, this requires an enormous amount of discipline by the patient to comply with the treatment regiment, see for example, U.S. Pat. No. 6,214,379, which is incorporated herein by reference. As illustrated earlier, to achieve optimal results, many patients may need to wake up during the night to take their medication. Hence, what is needed is a non-invasive, reliable means of delivering drugs compounds in precisely timed and measured doses-without the inconvenience and hazard of injection, yet with improved performance as compared to orally delivered drugs.

Addressing patient compliance (taking the proper dosages at the prescribed times) is another critical problem facing caregivers and pharmaceutical firms alike. Studies show that only about half of patients take medications at the times and in the dosages directed by their physician. It is reported that each year, 125,000 deaths and up to 20% of all hospital and nursing home admissions result from patient noncompliance. It is estimated that non-compliance results in additional healthcare costs in excess of $100 billion per year in United States. These figures are even more pronounced for the elderly.

An individual's failure to comply with a dosing regimen, e.g. failure to take one or more doses of a drug or taking too many doses, will have an adverse impact upon the success of the regimen. Individuals may fail to comply with their drug dosing regimen for a number of reasons. For example, drug dosing regimens, such as every 4 hours, e.g., 8, 12, 4, 8, 12, and 4 and the like, involve a rigid dosing schedule that may be incompatible with an individual's personal schedule. Such a rigid dosing schedule when combined with normal human traits such as forgetfulness or denial of a medical condition, as well as a busy life, represent substantial obstacles to compliance with a drug dosing regimen. Accordingly, such rigid dosing regimens often result in the failure by an individual to take one or more doses at the prescribed time. This has an adverse impact on the levels of the therapeutic substance at the active site and consequently on the overall efficacy of the therapeutic substance.

Hence, a need exists for systems and methods that increase patient compliance for administration of a variety of drugs. Also, there remains a need for an improved patch-based (or membrane-based) delivery system for an active substance that is able to administrate the delivery of a chemical substance to a subject over a period of time in a controllable way. It is a preferable for such a system or device to administrate the delivery of a chemical substance in a pulsatile and scheduled manner, pursuant to a pre-programmed dosage delivery regimen, meaning dosage sizes and times can be automatically varied according to such pre-programming.

SUMMARY OF THE INVENTION

Embodiments of the present invention provide a patch/drug reservoir-based transdermal delivery device to administrate the delivery of an effective substance to a patch or other drug reservoir adjacent to the membrane or in close proximity to the skin for transdermal absorption that absorbs or is filled with the substance (the administration reservoir) over a period of time or from time to time in a controllable and/or automated and programmable way. Significantly, these transdermal delivery devices include a reusable, active portion that includes a control and display unit and an active dispensing mechanism, e.g., a micropump that is in some embodiments a specially configured peristaltic pump, a pressurized reservoir, or other actuator. Further, the transdermal delivery devices include a detachable and disposable passive portion that includes a drug reservoir that is separated from the administration reservoir and holds the drug until the micropump or other actuator places the drug into the administration reservoir for transdermal absorption and a coupling mechanism/assembly for mating with the active dispensing mechanism, e.g., when the active dispensing mechanism is a peristaltic pump the coupling mechanism may include one or more elongate feed chambers (e.g., flexible tubes) that are connected to the drug reservoir and, in many cases, to the administration reservoir adjacent the membrane or skin or other material in contact with the skin. The coupling mechanism may be defined in part by the outer surfaces of a housing for the passive portion, and these surfaces may include grooves or guides for receiving and supporting the active dispensing mechanism. In some cases, the outer surfaces of the housing define an arcuate surface upon which the feed chamber or tube is disposed such that the shoes or other portions of the peristaltic pump can compress the tube to move liquid from the dispensing reservoir to the administration reservoir near the semi-permeable membrane or patch.

In addition, in the context of automated transdermal pulsatile drug delivery, starting dosing or bringing the active compound into contact with the skin may be only one part of the necessary methodology. The other part of the methodology may be to stop dosing or to stop permeation of the active compound through the skin. Stopping dosing automatically is extremely useful in certain situations to start and stop dosing so as to achieve programmed pulsatile drug delivery. The present invention not only has initial dosing or delivering methodologies, but also methodologies to stop dosing or permeation so as to deliver and stop delivering compounds to the body in a controlled and/or automated and/or programmable manner.

More specifically, in certain embodiments where the stoppage of permeation or dosing is desired, the active drug formulation or solvent is removed from the administration reservoir to stop dosing and/or decrease or end drug permeation through the skin. In this embodiment, a drug and/or solvent removal means is introduced (solvent/drug removal means). In this situation, either the above mentioned micropump or actuator (which may move gas or air) or a second micropump or actuator (which may move gas or air) will act to remove, and/or flush the active drug formulation or residual drug formulation/and or solvent from the administration reservoir into either into a waste reservoir or other area for evaporation or other removal. The first or second micropump or actuator, as applicable, may flush the administration reservoir with air, gas, inactive solution and/or a combination of these.

It is important to note that such an administration reservoir acts as the administration depot for the transdermal absorption and has a side (or a series of holes or openings or otherwise) that allows the drug formulation to come into contact with the skin for transdermal absorption, either by passing through a membrane in contact with the skin or otherwise to reach the skin for transdermal absorption. Such administration reservoir may take many forms, such as a substrate including a plurality of micro-passageways for the drug formulation; a substrate made up of micro-structured and/or micro-fabricated reservoirs; a substrate with a series of miniaturized or micro-structured reservoirs, a substrate including a plurality of ducts, culverts, and/or canals that may take any size, shape, or configuration and which may be micro-fabricated through any number of techniques including etching. This administration reservoir in whatever form it may take may be filled using a micro-pump or other type of actuator to allow for the transdermal absorption. The reservoir may then be flushed or emptied, so as to stop or slow drug delivery by removing the active drug from a position where it can access the skin for transdermal absorption. A heating element may also be present whether directly formed in the substrate forming the administration reservoir or as a separate component of the drug reservoir either at the top, bottom, or side of the drug reservoir. This heating element serves to increase the temperature of the skin surface which increases the permeation of the active compound through the skin. This heating element aids in the movement of liquids through the passageways, if applicable, including the administration reservoir. The heating element may also aid in the evaporation of the drug formulation where evaporation is a desired method to dry the administration area to stop dosing by causing evaporation. This heating element may be programmed to automatically heat the skin at precise preprogrammed times for precise timing of permeation enhancement and/or precise timing of stopping of dosing by inducing evaporation. The heating element may be configured with a plurality of flow paths for vapor or evaporated portions of the liquid (such as solvent vapor) that facilitates relatively uniform or at least well distributed flow away from the reservoir.

A further embodiment that requires the stopping of dosing induces evaporation of the drug formulation or more specifically, the solvent, from the administration reservoir so as to dry the administration reservoir which will result in the stopping of dosing. A dry skin/administration reservoir interface is not conducive to transdermal permeation. In this embodiment, the administration reservoir has vents or other accesses either to the environment for evaporation or immediate access by being in close proximity to a chamber(s) containing a desiccant. This desiccant chamber acts to induce evaporation and captures the solvent vapors to dry the interface and stop dosing. In this embodiment, the heating element, which may be programmed to heat at a certain time, heats the administration reservoir and/or skin and/or the whole device which increases significantly evaporation and speeds up the process which in turn stops dosing quickly. As an alternative to heat, a gas or air cartridge can be present to automatically, pursuant to a programmed schedule, blow air or gas onto the administration area to rapidly dry the administration reservoir and stop dosing.

The inventive system or device allows for pulsatile transdermal drug delivery, and the administration of differing sized dosages at different times of the day automatically, pursuant to a pre-programmed dosage profile (e.g., a program stored in memory accessed by the control unit). This system or device can be most advantageous when the pre-set or programmed drug delivery profile corresponds to desired peaks and troughs in disease symptoms based on chronobiology and a person's circadian rhythms. This system or device can also be highly advantageous in addiction management when programmed to coincide with a person's peak addiction cravings. This system or device can also be highly advantageous when patient compliance with a particular delivery regimen is a desired effect so that a person, whether forgetful, elderly, children, mentally impaired desires to ensure correct drug delivery compliance. This device can also be highly advantageous when a person or physician a doctor wants to have a drug administered in differing dosages while asleep automatically without the need to wake up, of if the drug being used is a stimulant and the person does not want any drug released at night thereby causing sleep disturbances, but does want the device to administer drug shortly before waking so that therapeutically effective blood plasma concentrations of the drug are present upon waking.

According to some embodiments of the present invention, the device comprises a control and display unit, a dispensing mechanism, e.g., a pump, pressurized reservoir or other actuator, a drug reservoir, an administration element, and/or a solvent/drug removal means (e.g., flushing the administration reservoir or using a desiccant or evaporative means such as heat or air/gas blowing to dry the administration reservoir), and/or a vapor removal element, when applicable, to the embodiment a waste reservoir, and/or an additional micropump or actuator. Embodiments of the invention may include one or more of the following features. The pump may be a peristaltic pump that includes a micromotor, a roller, a mounting plate, a tubing, and a housing. As discussed above, the peristaltic pump is separated into two parts; the first part comprises the motor on the mounting plate and the roller (e.g., provided in the reusable portion of the device) and the second part includes the tubing and the housing (e.g., provided in the detachable and disposable passive portion of the device). The micromotor and the roller are mounted in the device with the control unit. The speed of the micromotor is controlled by the control unit, so that the turning speed of the roller is controlled which, in turn, controls the flow rate from the dispensing reservoir to the administration reservoir. The tubing and the housing are detachable from the device.

Embodiments of the invention may include one or more of the following features. The tubing and the housing of the peristaltic pump and the dispensing or drug reservoir are combined together, resulting in one, interconnected disposable and replaceable dosing element. In other words, this disposable dosing element (or detachable and disposable passive portion) is a replaceable dosing capsule which can be used for one or multiple dosings. This disposable dosing capsule can be "snapped" into place prior to substance administration by the patient or other health worker, and, after the drug reservoir is exhausted, the disposable dosing element is "popped" out to be disposed, and a fresh disposable dosing element is then "snapped" back into the device. The tubing is provided inside the body of the capsule in some embodiments. One end of the tubing is connected to the drug or dispensing reservoir while the other end of the tube is a fluidic adapter or distributor near the administration reservoir or area near the patch or membrane. In certain embodiments, the waste reservoir, desiccant chamber capturing vapors evaporated from the drug/solvent, tubing and analogous components of the second micro pump or actuator as the first pump mentioned above, a gas/air cartridge and the administration reservoir may also be part of this snapped on or snapped off portion or may be disposable pursuant to another means. Further, embodiments of the invention may include one or more of the following features. The disposable dose capsule, the administration element, and a drug/solvent removal element are connected and packed together as a disposable package, whenever the dosage is needed to applied to skin, the whole disposable package is changed and replaced into the device.

More particularly, an apparatus is provided for selectively delivering a liquid, powder, or temporarily free-flowing solution (e.g., a drug formulation or the like). The apparatus includes an active assembly with a controller and a power source (e.g., a battery). The apparatus further includes a passive assembly configured for mechanically coupling and decoupling with the active assembly. The passive assembly includes a drug reservoir containing the drug formulation to be delivered. The apparatus further includes a micropump or other actuator that acts as the dispensing mechanism with an active portion in the active assembly that provides a motive force to draw or otherwise move the drug formulation from the drug reservoir onto or into the administration reservoir. The micropump or other actuator (or dispensing mechanism) includes a passive portion provided in the detachable passive assembly so as to be proximate to the active portion of the micropump/actuator. The passive portion defines a feed or delivery chamber through which the drug formulation flows from the drug reservoir when the motive force is applied to the passive portion. In some embodiments, the micropump or other actuator includes a peristaltic pump with the active portion being made up of: a motor powered by the power source and operated by the controller to control the motor speed and its time of operation; a roller with rotatably mounted shoes; a shaft contacting the roller and driven by the motor; and a mounting plate supporting the motor. The passive portion, in turn, includes a housing with a guide slot or recessed surface for receiving the mounting plate and roller so as to position one or more of the shoes in contact with an outer surface of the feed chamber, which in some embodiments is a length of compressible tubing. The guide slot in these cases may include a curved surface and the tubing is positioned between the roller/shoes and the curved surface such that the motive force includes using the shoes to sequentially compress the tubing.

The passive assembly may further include an administration assembly including an administration reservoir connected to the tubing to receive the drug formulation and a membrane adjacent the administration reservoir that is permeable to an active or effective substance in the drug formulation but not or less permeable to a solvent portion of the liquid. In certain embodiments, an absorbent sheet (e.g., blotting paper or the like) may be provided in the administration reservoir so as to distribute the received liquid in a relatively uniform manner over the surface of the membrane. In other embodiments, instead of an absorbent sheet, the administration reservoir may be or include a rigid or flexible, permanent or disposable substrate with a plurality of ducts, conduits or culverts that contain internal passageways for movement of the drug formulation and have either a series of openings or a single opening mounted on the membrane or skin or otherwise adjacent to the membrane or skin to allow the drug formulation to be absorbed or otherwise transferred or to move from the substrate ducts to the membrane or skin for transdermal absorption. In this manner, the ducts, conduits, or culverts or in this substrate can be filled by the micropump or other actuator with drug formulation originating in the drug reservoir. Then, these ducts, conduit, or culverts can be flushed either by the first micropump actuator or a second micropump or other actuator into a waste reservoir or flushed into an area for evaporation to begin and stop dosing in an accurate fashion. Yet further, a heat element may be provided in the administration assembly near the administration reservoir to raise the temperature 3 to 10 degrees Celsius over a dermal temperature to enhance transdermal permeation and/or diffusion and/or movement of the drug formulation through the substrate and in some cases to increase evaporation when it is desired to dry the reservoir (or absorbent sheet). In the latter instance, the heating element may be configured with a plurality of flow paths for vapor or evaporated portions of the liquid (such as solvent vapor) that facilitates relatively uniform or at least well distributed flow away from the reservoir.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

DETAILED DESCRIPTION OF THE PREFERRED EMBODIMENTS

Figure 1:
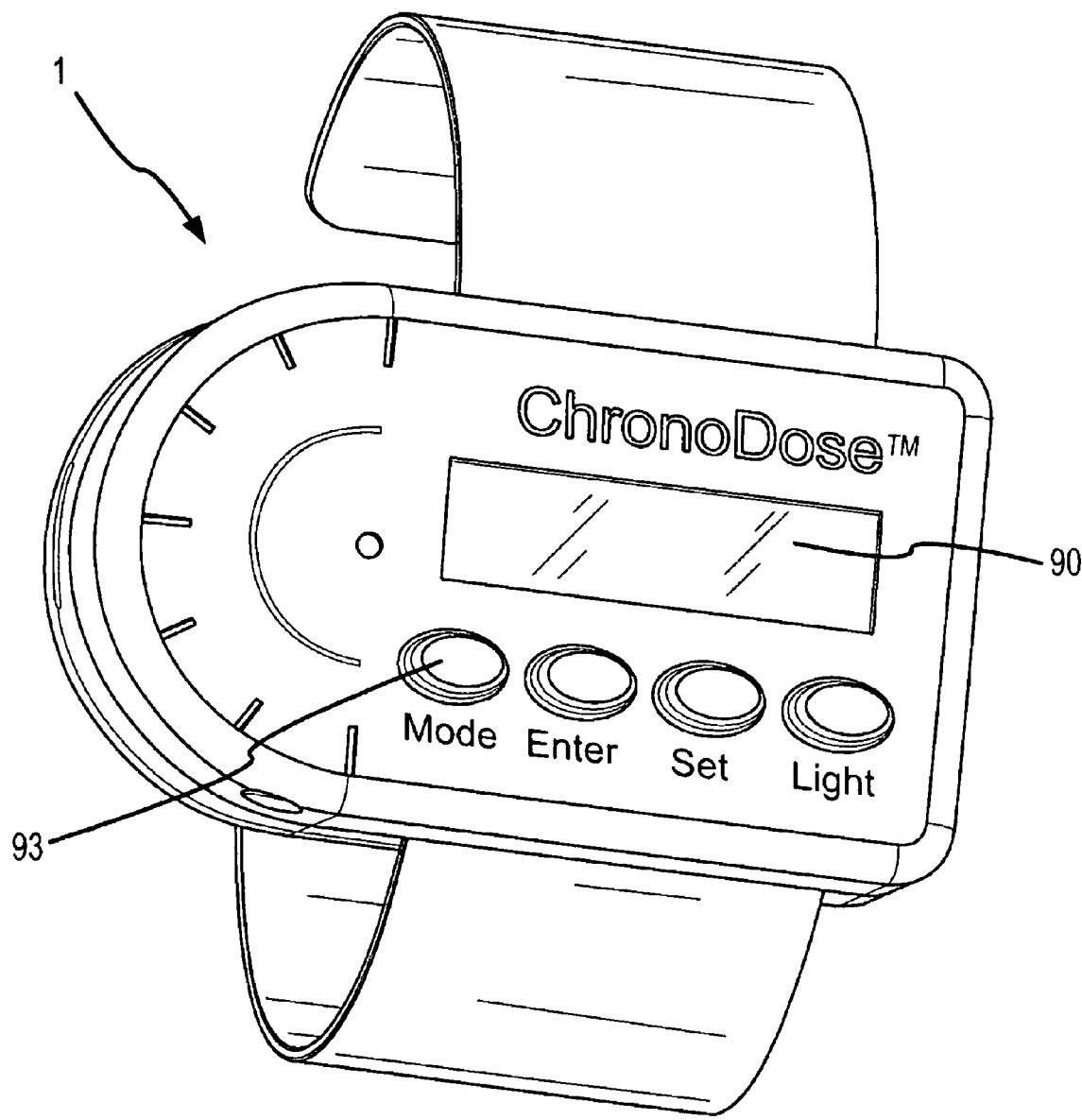
FIG. 1 is a perspective view of an exemplary portable transdermal drug delivery device or assembly of the present invention.

In the drawings, like reference numerals indicate like features, and a reference numeral appearing in more than one figure refers to the same element. The drawings and the following detailed descriptions show specific embodiments of the invention with numerous specific details including materials, dimensions, and products being provided to facilitate explanation and understanding of the invention. However, it will be obvious to one skilled in the art that the present invention may be practiced without these specific details and these broader embodiments of the invention are considered within the breadth of the following claims.

The present invention is generally directed to a portable drug delivery device that can controllably deliver a particular dose accurately and in a timed manner. The devices of the invention are typically configured with a reusable portion and a disposable portion. The reusable portion typically includes the display and control components such as a microprocessor, memory, interfaces, and power source and also includes the active portion of a dispensing mechanism (e.g., active portion of a micropump). The disposable portion can be selectively coupled or attached to the reusable portion and includes the passive portion of the dispensing mechanism (e.g., a micropump housing and feed or delivery chamber/tubing) as well as the drug or dispensing reservoir and also the administration assembly that may include an administration reservoir, a diffusion membrane, and a solvent removal element. In this manner, the present invention addresses problems with a membrane having a decreasing diffusivity that may be caused by saturation with solvent, the contact surface becoming dirty or clogged, or other factors. The device also facilitates the reuse of more expensive components such as the microprocessor, memory components, a liquid crystal display (LCD) or other display, and active pump portions. These and other unique features of the invention will become apparent in the following description.

FIG. 1 illustrates one embodiment of a portable drug delivery device or assembly 1 of the present invention. The device 1 is shown to generally take the form of a wrist watch for easy attachment to a patient's arm or wrist to place an administration element and more specifically a diffusion membrane for transdermal delivery (or, in some cases, a needle for subcutaneous delivery), e.g., an administration assembly that can be removed from the reusable portion of the device 1 shown in FIG. 1 is provided on the underside or reverse side of the device 1. The device 1 includes a display 90 to allow a patient or user of the device 1 to obtain a status of a dosing regimen, e.g., to know whether the device 1 actively dosing, when a next dose may be administered, how many doses remain for the device based on the particular disposable dosing element, or the like. An input area or keyboard/keypad 93 is provided to allow the user to alter the display 90 and otherwise interact with the device 1.

Figure 2:
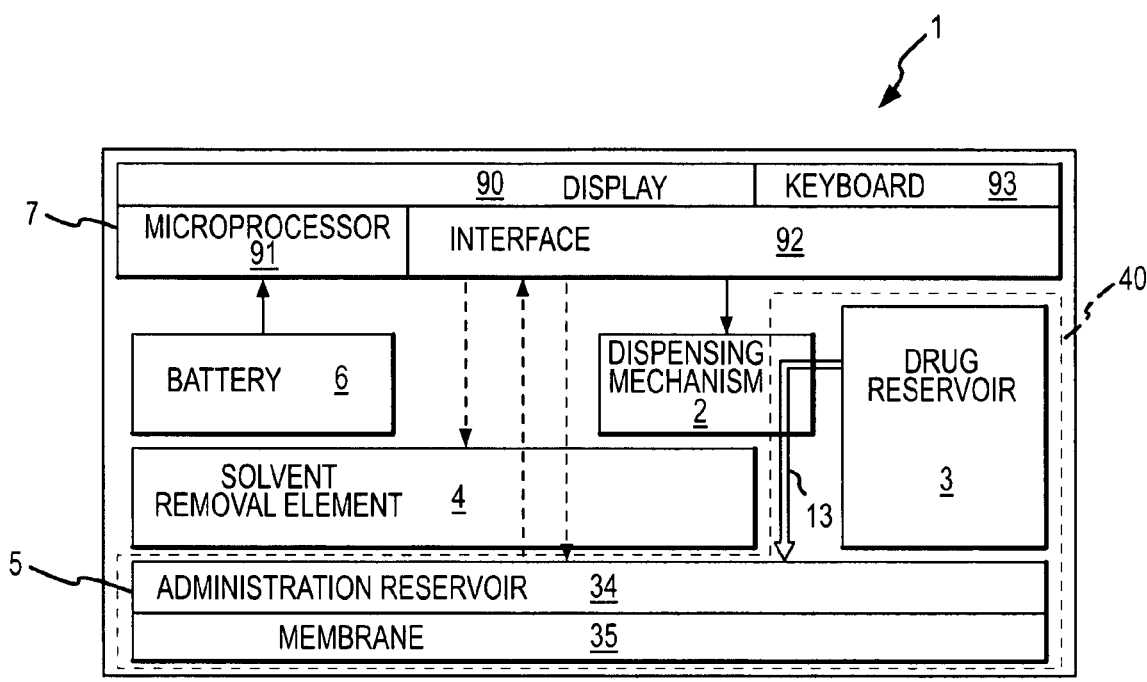
FIG. 2 is a block diagram of the drug delivery device of FIG. 1 showing in block form representative components of a portable device for transdermal drug delivery.

FIG. 2 illustrates in block form the components of the device 1 in one embodiment of the invention. The portable device 1 as shown is configured for transdermal drug delivery and includes a control and display unit 7, a dispensing mechanism 2, a drug reservoir 3, an administration element 5, a solvent removal element 4, and a battery 6. A liquid is typically provided in the drug reservoir 3 for dispensing via feed chamber or delivery tube 13. The liquid includes a sufficient or predetermined amount of one or more active substances dissolved or dispersed at an appropriate concentration in a formulation which contains a solvent (or more volatile liquid) or a mixture of solvent along with the active substances. For example, the solvent may include one or more agents such as alcohols, oils, water, methylene chloride, ethanol or the like. If appropriate, other excipients may be provided in the reservoir 3 such as tissue permeation promoter (enhancers), thickening substances, solubizers, buffers, chemical stabilizers, preservatives, moisturizers, humectants, emulsifiers, thinners, surface-active agents, fragrances, or the like. Examples of active substances include, but are not limited, to nicotine, steroid hormones, analgesics, antioxidants, vitamins, CNS drugs, cardiovascular drugs, anti-asthmatics, antibiotics, anti-cancer drugs, and the like and the invention is intended to cover any drug or other substance for which it is desirable to provide to a patient or other body (animal or human) in a time and dose controlled manner.

The control and display unit 7 can be implemented, for example, by a microprocessor 91 with a LCD or other display 90 and a drive circuit and/or interface 92. The microprocessor 91 is programmed (with software, such as a dosing regimen routine or the like, in memory for example) as a programmable timer to send a control signal to the dispensing mechanism 2 through the drive circuit 92 at multiple timing points. Battery 6 provides power to the device 1. In a specific embodiment, the dispensing mechanism 2 is a two-part peristaltic micropump (e.g., a peristaltic pump with an active portion that is provided with reusable portion of device 1 and a passive portion that is provided with detachable and disposable portion 40) that delivers a drug formulation from the drug reservoir 3 to the administration element 5 at a certain flow rate and a certain duration that are defined by the microprocessor 91 of the control and display unit 7.

In some embodiments, the drug reservoir 3 is in form of a collapsible balloon that contains drug formulation. A flexible and collapsible reservoir 3 is preferable in the device 1 to avoid back pressures that may resist flow from the reservoir 3 if a more rigid-walled reservoir were utilized. The walls of the reservoir 3 are also preferably resist permeation, i.e., are non-permeable or relatively impermeable, of the solvent/drug mixture or formulation and in this regard, the walls may be formed of Teflon™, a high molecular membrane, or other similar material.

The administration element 5 is typically provided in the disposable, detachable portion or unit 40 to allow it to be periodically replaced with a new element 5. This is useful for providing a new membrane to achieve a known diffusion rate and to provide a new administration reservoir (and any wicking material or the like provided in such an administration reservoir as discussed below). As shown, the administration element 5 includes an administration reservoir 34 and a diffusion membrane 35 (e.g., a membrane that allows a particular diffusion rate for the drug in the liquid or mixture in the drug reservoir 3 but is impermeable or much less permeable to the solvent).

As will be discussed in detail, one aspect of the invention is the inclusion of material, such as blotting paper or sheet, in the reservoir 34 to uniformly distribute the formulation to the diffusion membrane both in volume (e.g., the liquid is relatively equally provided over the upper surface of the membrane rather than much more at the outlet of the feed or delivery chamber/tube 13) and at a relatively uniform rate. For example, in one embodiment, the administration element 5 includes an absorption sheet (e.g., blotting paper or the like to "wick" the liquid from chamber or tube 13 over the administration reservoir 34) and a membrane which are laminated tightly together at their interface and typically to the edges of the frame of the element 5. The particular membrane used for membrane 35 is not limiting and may include, but is not limited to a membrane of microporous polyethylene, polyethylene co-vinyl acetate (EVA copolymer, polyurethane, and the like. A device-skin interface coupling media and/or control membrane or layer may further be provided of ethylcellulose, hydroxypropyl cellulose, poly(ethylene co-vinyl acetate), polyvinyl pyrrolidone, poly(ethylene oxide), poly (ethylene vinyl alcohol) and the like.

Tubing or a feed chamber 13 is provided in the detachable and disposable unit 40 to connect the drug reservoir 3 to the administration element 5 through passive portion of the dispensing mechanism 2. When the device 1 is positioned for use, the membrane 35 is preferably in tight contact with the skin using an adhesive and/or wristband. The device 1 then operates to provide even diffusion of the drug over the drug absorption surface area of the membrane 35. A solvent removal element 4 is typically provided in the device 1 (e.g., in the reusable portion as shown or in the disposable portion in some cases) to control dosing by removing the solvent or fluid mixture. The element 4 may include desiccant, absorbent material, or other material to absorb evaporating solvent, with the element 4 being connected to the administration element such as by one or more tubes (not shown). A connection is shown between the interface or drive circuit 92 of control unit 7, and this may be used to sense the concentration of a drug in the administration reservoir 34 and to control operation of the solvent removal element (e.g., in embodiments where active components are provided to further solvent removal as discussed below). In some embodiments, these connections may also be used to allow the control 7 to receive temperature signals from a sensor contacting or near the reservoir 34 and/or membrane 35.

In some preferred embodiments, the dispensing mechanism 2 is a micropump, e.g., positive displacement micropump. For example, the pump 2 may be a two part piezoelectric micropump in which the drive or active portion is provided in the reusable portion of the device 1 and the chamber 13 is provided in the disposable portion 40. In one preferred embodiment, the micropump is configured as a two-part peristaltic pump that can be provided as an active part and a passive part to allow the active part to be provided in the reusable portion of device 1 and the passive parts including the tube or feed chamber 13 and portions of the pump housing (including the compression surface) provided in the detachable and disposable portion 40.

Figure 3:
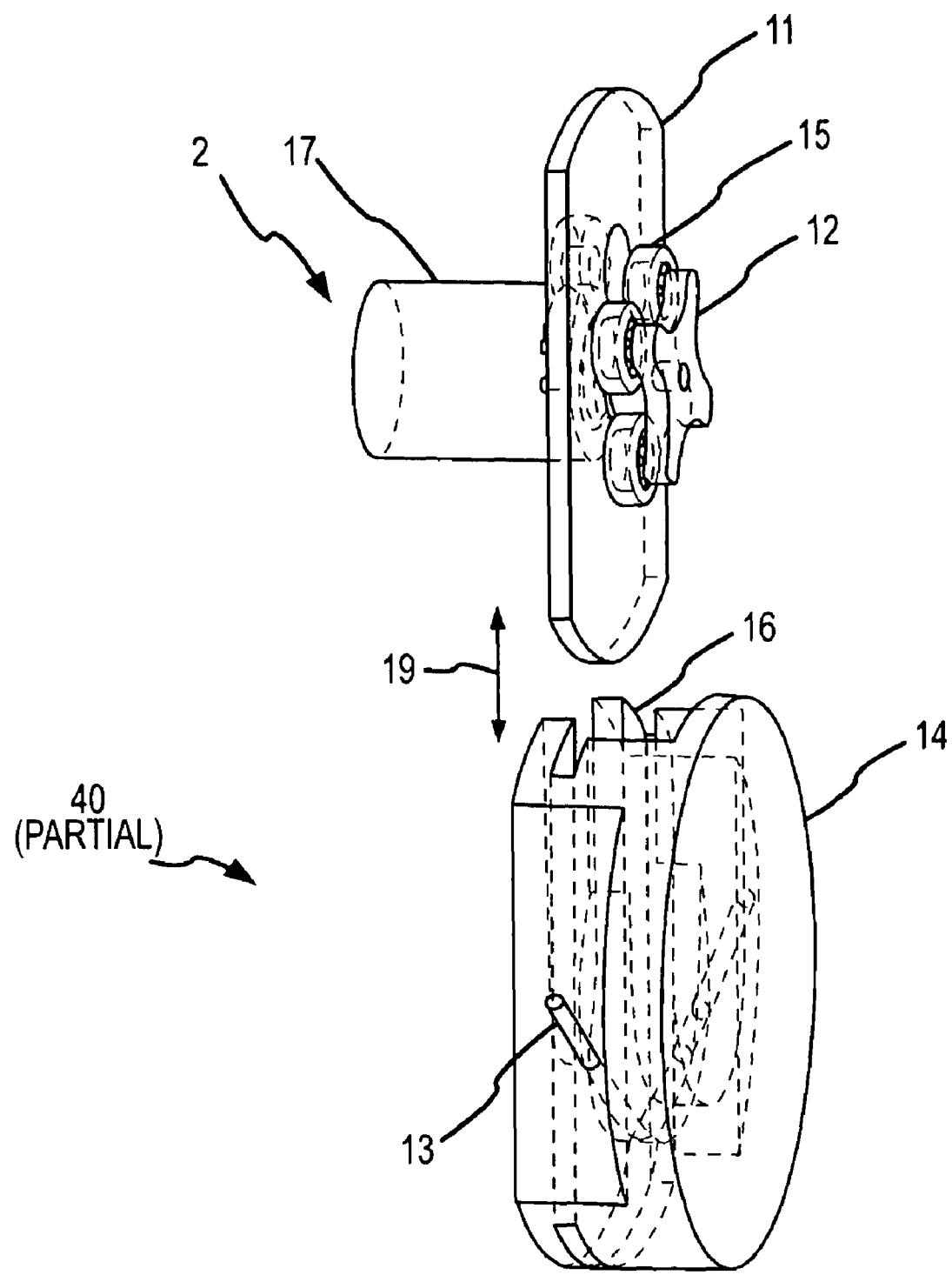
FIG. 3 is perspective view showing some of the components of the active and passive portions of a portable drug delivery device in a disassembled arrangement (e.g., prior to attachment of a dosing element with its drug reservoir and receiving slot or channel and tube/delivery channel to a reusable active element or portion (e.g., active portions of a peristaltic pump))

According to one representative embodiment, FIG. 3 shows a disassembled peristaltic pump for use as dispensing mechanism 2. The pump 2 has two parts or elements: an active part and a passive part. The active part is an assembly of a motor 17, a mounting plate 11, a roller 12 attached to a shaft of motor 17, and shoes 15, which are rotatably mounted to roller 12 and are shown as four ball bearings (but two or more shoes 15 may be used and other configurations other than ball bearings may be used to practice the invention). The active part is preferably housed with the other components of reusable portion of device 1 such as the battery 6 and control and display unit 7, such as with the plate 11 and drive components 12 and 15 being exposed with the motor 17 being completely or partially inserted into the housing wall (not shown).

The passive part of the dispensing mechanism 2 is, in contrast, provided in the disposable portion 40 as shown in FIG. 1 and is designed or configured for coupling with the plate 11 and drive components 12, 15 of the active portion of the mechanism 2. The passive part is an assembly of a pump housing 14 and a tubing or feed chamber 13. A receiving slot or guide 16 is provided with an opening and internal surfaces (including an arched or arcuate compression surface 16A shown in FIGS. 4 and 5 on which the tube 13 is positioned for compression by the shoes 15) for receiving the active portion, e.g., receiving and supporting plate 11, rollers 12, and shoes 15 while allowing motor 17 casing to slide through the outer wall of housing 14.

The motor 17 can be a stepping motor or a DC motor that is speed-controlled by a control unit (such as control 91 via interface 92). The motor 17 is mounted on the mounting plate 11 that is fixed in a device, which is the device 1 in the embodiments of this invention and the plate 11 and part of the motor 17 may extend out from a housing (not shown) that houses the non-disposable components (i.e., the components that are not part of unit 40 in FIG. 1). The roller 12 is mounted on the axis or drive shaft of the motor 17. On the roller 12, there are four ball bearings 15. In the housing 14, there is a slot 16 that accommodates the motor 17, the mounting plate 11, and the roller 12. The tubing 13 is inserted through the housing 14 on which there are provided two holes. Tubing 13 passes through the holes.

FIG. 3 shows a cross sectional view of the peristaltic pump dispensing mechanism 2 in which the passive part is slid up so that it is positioned to where the bearings 15 on the roller 12 press against the tubing 13 properly and when rotated periodically compress the tube 13 against the arched or curved surface 16A. The tubing 13 is flexible so that the bearings 15 on the roller 12 press the tubing 13 against an arc 16A and move the fluid along through the tube 13. In this embodiment, the four bearings 15 on the roller 12 act as shoes to press on the tubing 13. Three to five or more shoes 15 can be used. When assembled in a portable drug delivery device, the tubing 13 connects the drug reservoir 3 to the administration element 5 in the application of the device 1 shown in FIG. 1.

The use of a peristaltic pump as the dispensing mechanism 2 provides significant advantages for a drug delivery device according to the invention. These advantages include low risk of drug formulation contamination as the drug only contacts the tubing and not the drive components of the pump 2 and this tube 13 is disposed of with the disposable unit. The use of a peristaltic pump 2 also provides simple and cost-effective operation, accuracy of dosing, low maintenance, self-priming, and gentle pumping action, as well as the ability to pump liquid, mixed-phase and viscous fluids, and the elimination of the need to clean or flush the pump or tubing of substance residue, to ensure sterility of the device over period of time. One of the chief advantages of the peristaltic pump 2 for the drug delivery device 1 is that the drug formulation from the drug reservoir 3 to the administration element 5 does not contact any internal parts. Seals and valves are not needed as in other pumps.

Figure 5A:
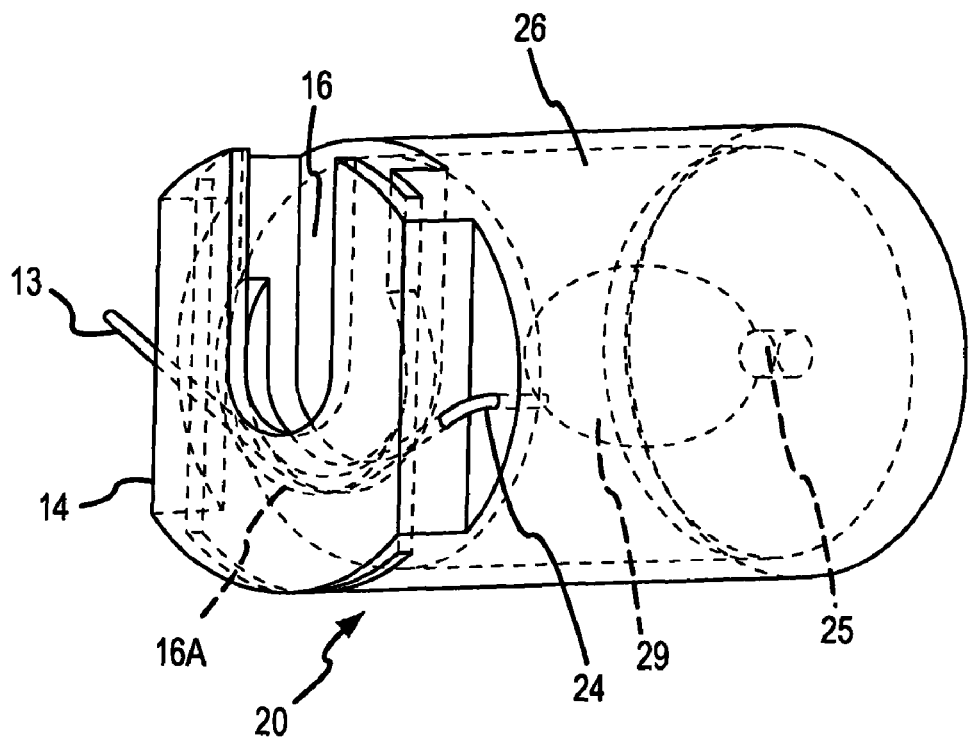
FIGS. 5A, 5B, and 5C are perspective and schematic side views of an embodiment of a dose capsule with a drug reservoir and a housing for a peristaltic pump.
Figure 5B:
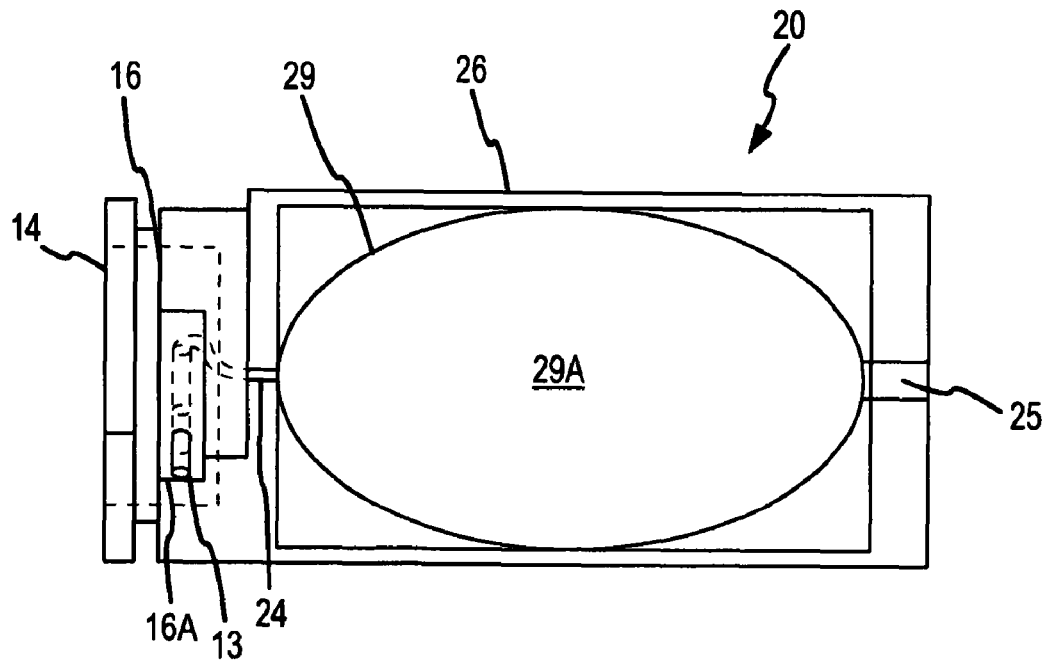
Figure 5C:
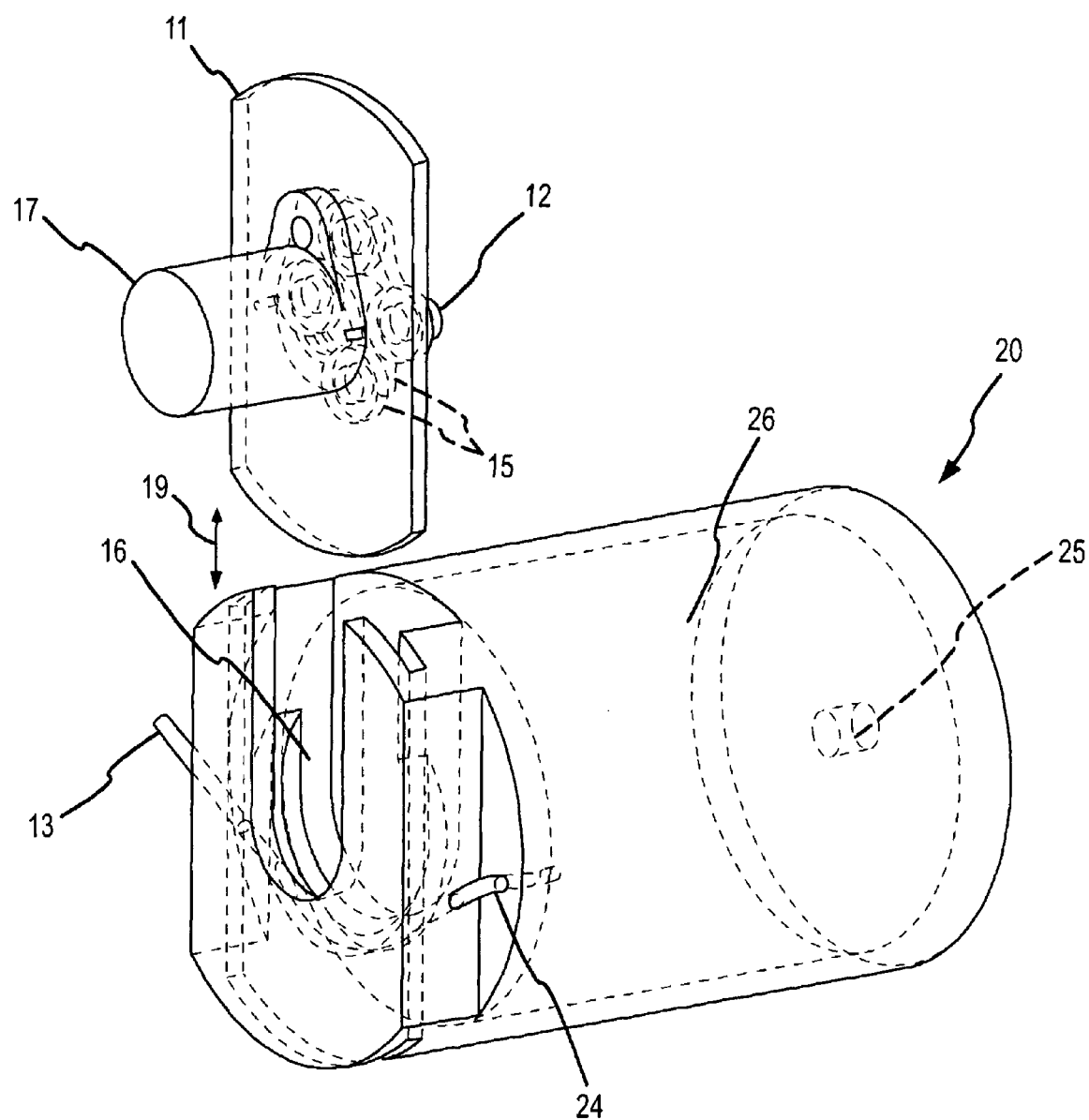

FIGS. 5A-5C show one preferred embodiment of a dose capsule 20 with a drug reservoir 26 and a peristaltic pump housing 16 (e.g., the passive portion of the dispensing mechanism 2). Inside the drug reservoir 26 there is a collapsible balloon 29 with an inlet 25 and an outlet. The inlet 25 is connected to a fluidic fitting for drug formulation pre-loading (e.g., filling of the balloon or flexible, collapsible reservoir 29). The outlet is or connected to internal tubing 24, which is pulled through the housing 16 to compose a peristaltic pump 2 with tubing 13 (e.g., internal tubing connected to reservoir, tubing in contact with shoes 15 and surface 16A, and external tubing that extends out from housing 14 to connect with an administration or delivery assembly or element (such as element 30 of FIG. 6).

By combining the peristaltic pump housing 16 with the drug reservoir 26 (both of which are typically formed of a rigid plastic or the like), the dose capsule 20 can be a disposable element separately or with the delivery element, as discussed below. When the drug formulation is replaced, the tubing 13, 24 of the pump 2 is also simultaneously replaced. The design of the present invention minimizes or eliminates the need for cleaning the peristaltic pump of the device. Another main practical advantage of this design is to avoid shelf-time problems of the device. If the peristaltic pump is assembled with the housing and the tubing, the shoes on the roller will press against the tubing for a long period of the shelf time, which may result in tubing deformation problems and affect the accuracy of the flow rate of the peristaltic pump. If the drug reservoir and the peristaltic pump are not assembled together as shown and described, it may be inconvenient for a patient to change the drug formulation because the disconnection and connection of the tubing with the drug reservoir, and priming the pump are not user friendly and easy tasks. Our embodiment separates the peristaltic pump into two parts, the active and passive parts, in order to retain the expensive active part of the peristaltic pump in the device and combine the passive part with the drug reservoir. This approach of the two components minimizes or eliminates the problems detailed above.

FIG. 5C shows an embodiment of this invention with the passive portion of the dispensing mechanism 2 disassembled from the active part. The active part of the peristaltic pump, i.e., the motor 17, the mounting plate 11, and the roller 12, is retained in the device (e.g., device 1 of FIG. 1) and is not typically disposable (e.g., is reusable). The passive part, i.e., the peristaltic pump portions including the housing 14, the receiving slot or guide 16, and the tubing 13 and 24, is combined with the drug reservoir 26 with fill connection 25 to form the disposable dose capsule 20 which is replaceable as shown with line 19. The end of external tubing 13 is connected to an administration element (such as shown in FIG. 6) for drug delivery from the reservoir 26.

Figure 6:
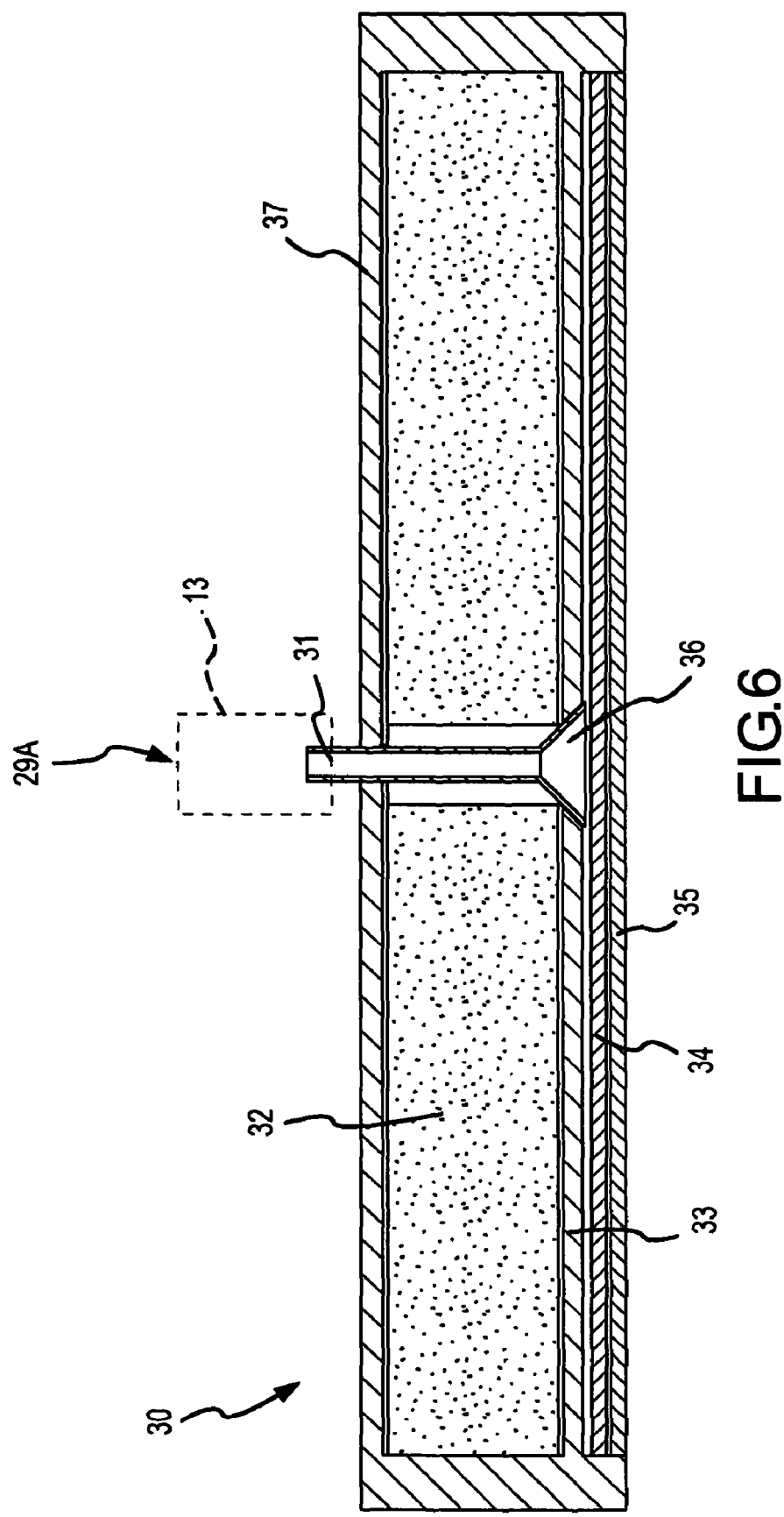
FIG. 6 illustrates a cross-sectional view of a delivery or administration element with an administration reservoir and a solvent removal system such as may be attached to the drug delivery chamber or tube from the passive portion of a dispensing mechanism such as those shown in the devices of FIGS. 3-5C, whereby the entire administration assembly may be attached, used for dosing for a period of time, and detached and disposed of after dosing is complete (and later replaced when appropriate with a new assembly)

FIG. 6 shows a cross sectional view of one preferred embodiment of a delivery element 30 for connection to tubing or feed chamber 13 to receive the drug mixture 29A from a flexible drug reservoir liner 29. Such connection of the element 30 and the dose capsule may be done by the user/patient or more typically, are done for the patient (such as by a dose supplier or manufacturer) such that the user/patient can simply "snap" off a used/depleted disposable unit or portion of a device and "snap" or connect a new unit including both a dosing capsule and the delivery element 30 (with this connection acting to couple the passive and active portions of the dispensing mechanism such as two parts of a pump).

As shown, the delivery element or assembly 30 includes a housing 37, a tubing or fill line 31 with an optional conic or funnel-shaped end 36. In this embodiment, a solvent removal element 32 (such as element 4 of FIG. 1) is provided in the element 30 so as to support solvent removal to control or end dosing. For example, a desiccant filling 32 may be provided in chambers of housing 37 as shown. A frame 33 defines an administration reservoir at one end of the housing (e.g., distal to the connection line 31) that can be filled with fluid 29A. To facilitate more uniform distribution of the liquid 29A, an absorption sheet 34 such as blotting paper or other material that functions to absorb and wick or transport the liquid 29A from conical outlet 36 about the area of the reservoir, is provided in the reservoir (or to define the administration reservoir by filling the reservoir chamber defined by frame 33).

The blotting paper or absorption sheet 34 acts to hold the liquid 29A to provide a more controllable diffusion rate for element 30 and typically the sheet 34 is "saturated" by selecting a volume of liquid 29A to wet the entire or substantially the entire sheet 34. The element 30 further includes a diffusion membrane 35 that typically abuts and may even be laminated to absorption sheet 34. The housing 37 with the frame 33 forms a chamber that is a solvent removing element 4 of FIG. 1, where the absorbent material 32 such as a desiccant filling is placed. The absorption sheet 34 and the diffusion membrane 35 are laminated together in some embodiments. The absorptions sheet 34 can be blotting paper, sponge, porous plastics, porous rubber, cellulose, or other materials (e.g., material with similar liquid absorbency and/or wicking properties), with a thickness in the range or 0.3 to 3 mm or more.

Drug formulation 29A is delivered by the dispensing mechanism 2 that is connected to the tubing or fill line 31. The conic end 36 of the tubing 31 may be contacted to the absorption film 34 or be spaced apart. The drug formulation 29A dispensed through the tubing 31 is soaked up by the absorption film or sheet 34. The diffusion membrane 35 is preferably, but not necessarily, in tight contact with the absorption film 34 on one side and with a patient's skin on another side (when in use), and provides an even diffusion of the drug over its surface area. The conic end 36 provides a larger absorption area, which facilitates distribution of the liquid 29A and also inhibits accumulation of the drug formulation at the end of the tubing and capillary action that draws the drug formulation back into the tubing 31 when the dispensing mechanism stops.

The solvent of the drug formulation evaporates continuously from the absorption film 34. Vapor is trapped by the desiccant 32 in the solvent removing element. Solvent removal serves the purpose of withdrawing depleted solvent from the absorption film 34 and the membrane 35, so that, after repeated dispensing no freely moving liquid is formed. The amount of drug delivered increases by increasing the volume of dispensed formula. Furthermore, by withdrawal of solvent in-between dispensing events, drug concentration steadily increases and reaches saturation or possibly super saturation in the absorption film 34 and the membrane 35, thereby maximizing delivery rate. When dispensing of the drug formulation is stopped the residual solvent in the absorption film 34 and the membrane 35 is removed by element 32. The absorption film 34 and the membrane 35 are dried which stops drug delivery.

Figure 4:
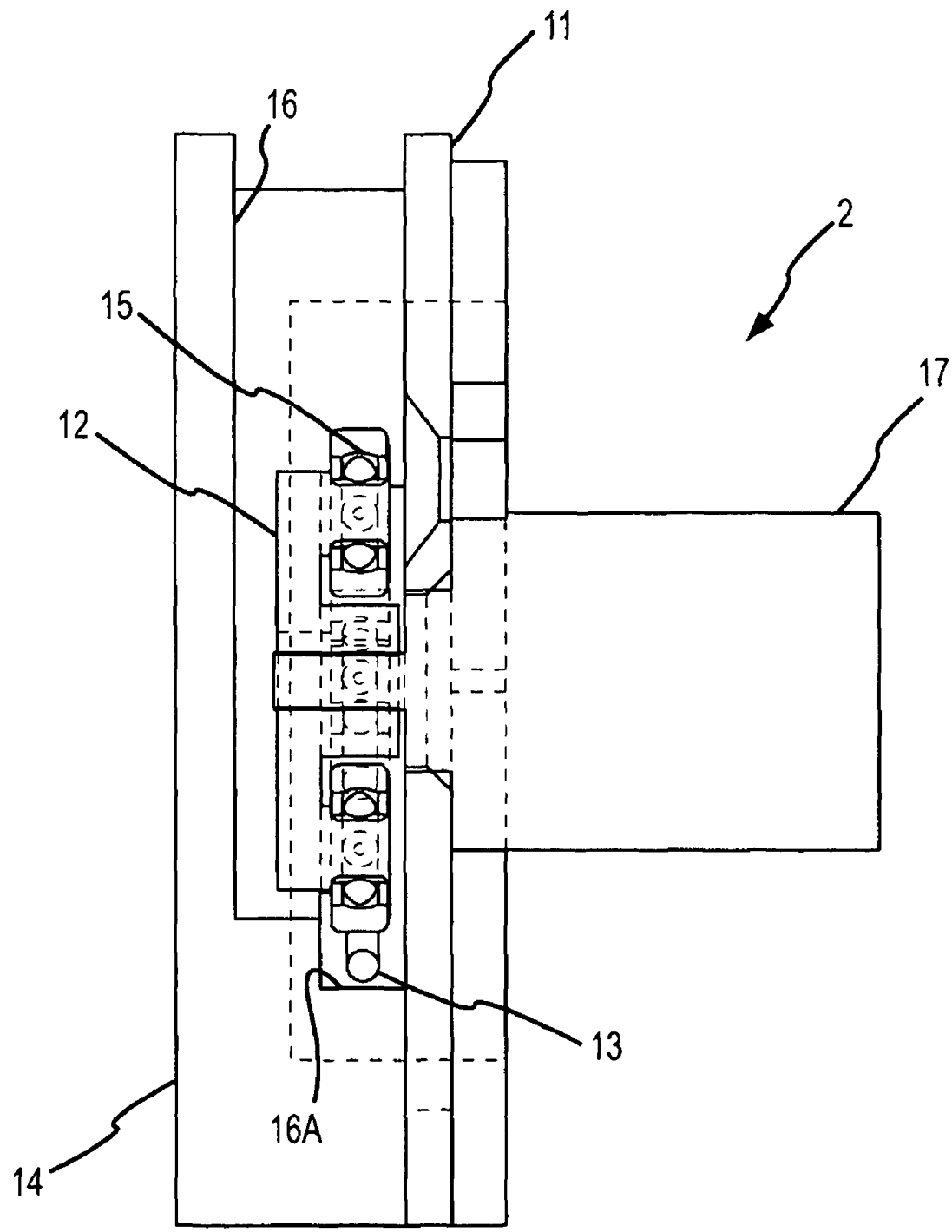
FIG. 4 is a cross sectional view of the assembled peristaltic pump of FIG. 3 showing mating or coupling of the active and passive portions (or reusable and disposable portions) of a portable drug delivery device.
Figure 7:
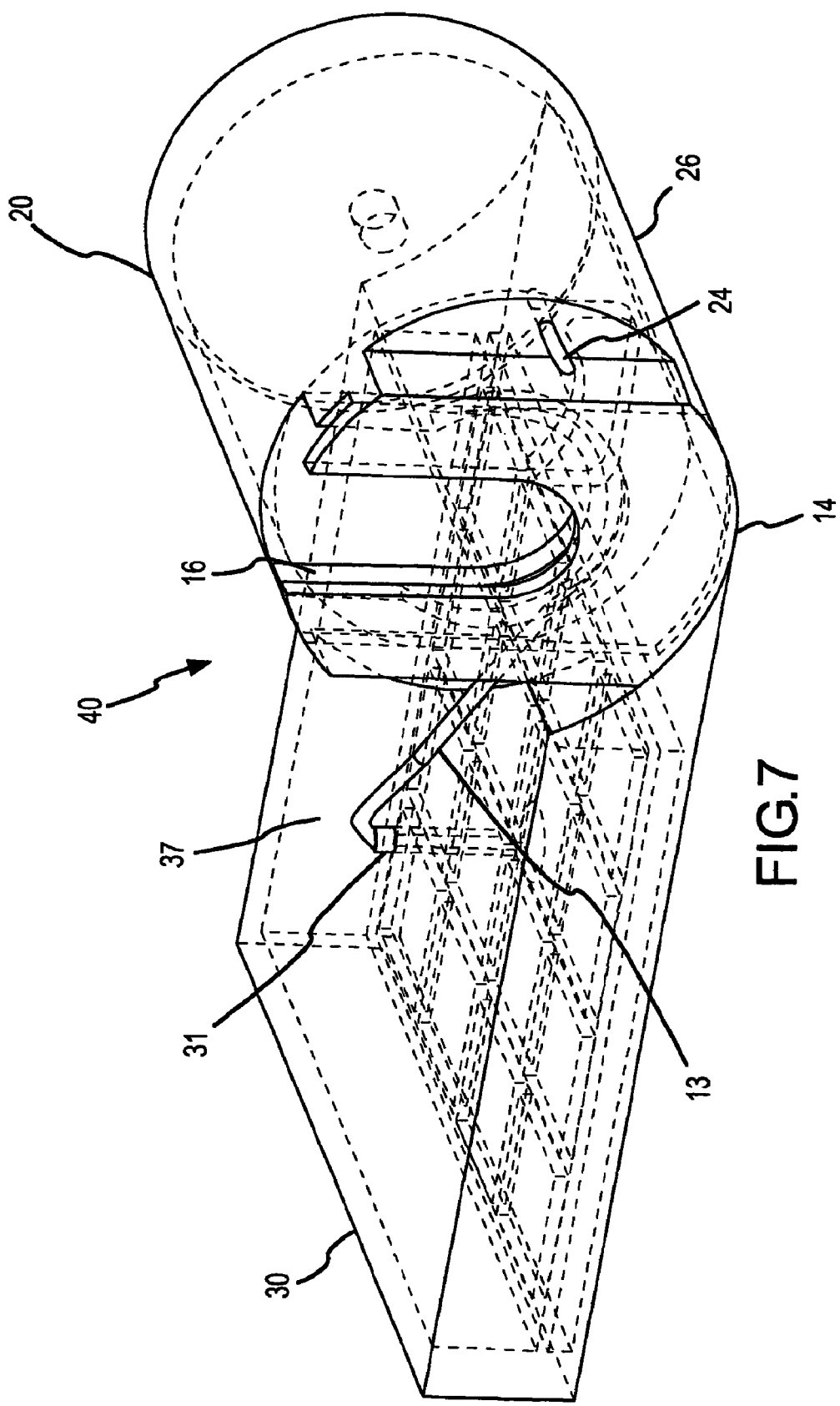
FIG. 7 is a perspective view of an assembled administration assembly made up of a delivery element and a dose capsule or element.

FIG. 7 shows a combination (e.g., a disposable and detachable portion) 40 of the delivery element 30 with the dose capsule 20 shown in FIG. 6 and FIG. 4, respectively. The disposable portion 40 may be an integral body of the dose capsule 20 and the delivery element 30 or may be two housings that are mechanically connected or fastened. Tubing 13 connects the internal tubing 24 in the dose capsule 20 for the peristaltic pump with tubing or fill line 31 in the delivery element 30. The combination 40 can be molded and assembled to be a package for one dose of a treatment or multiple doses of a dosing regimen. Drug formulation can be pre-loaded into the drug reservoir 26. The 13, 24 can also be embedded in the body of the combination of the delivery element 30 and the dose capsule 20. Whenever the drug formulation is replaced, the tubing, the desiccant, and the absorption and membrane are all replaced, so that the problems for the customer related to tubing disconnection and connection, desiccant replacement, and the absorption and membrane change are minimized or eliminated. Plugging the dose assembly or disposable portion 40 into the device 1 by connection of housing 14 with receiving groove 16 with the active portions of a dispensing mechanism or pump 2 as discussed above allows customers such as patients and medical technicians to easily operate a portable drug deliver device of the present invention.

Figure 8:
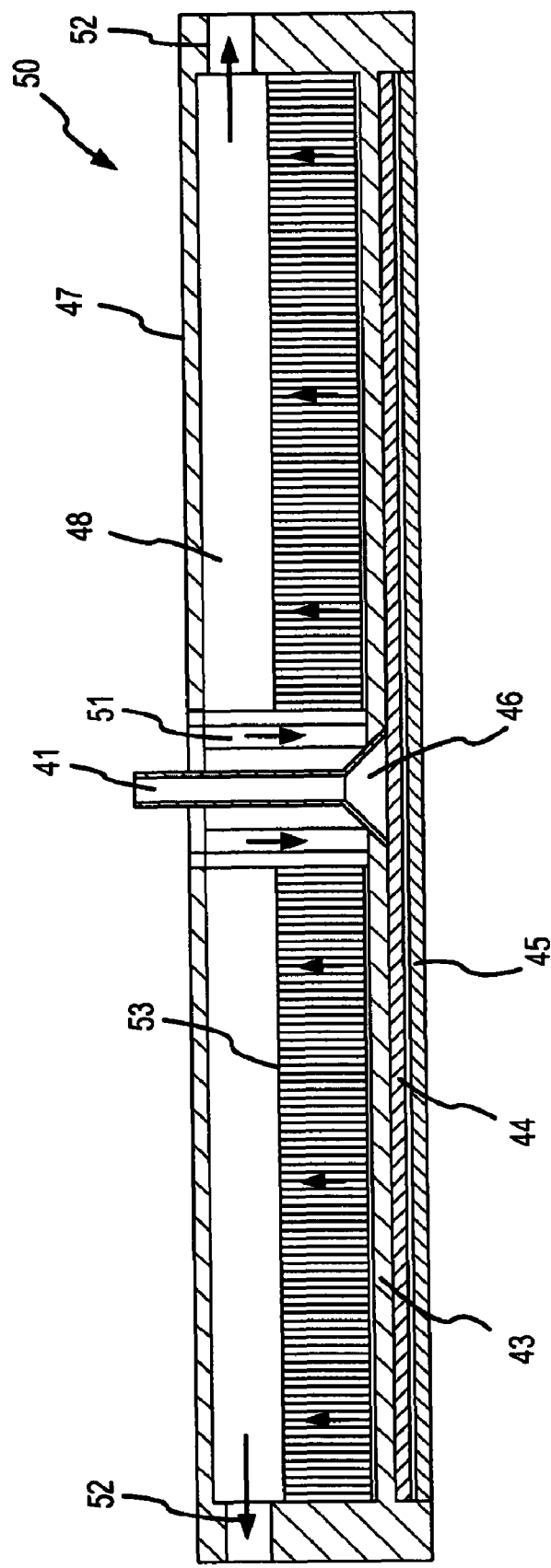
FIG. 8 is cross-sectional view similar to that of FIG. 6 showing an alternative embodiment of a delivery or administration element adapted for solvent removal via air or gas flow through the administration reservoir.

In a further embodiment of a solvent removal element 4, FIG. 8 shows a cross sectional view of an embodiment 50 that blows air or other gas onto an administration sheet 44 (or through an empty administration reservoir) to aid in the evaporation of solvent. The preferred embodiment 50 includes a housing 47, and a tubing adapter or fill line 41 with a conic end 46. In the reusable portion, a gas source or blower is provided (but not shown) that may include a pump/blower, a pressurized canister with a volume of pressurized gas, or the like as well as controls and valving as necessary to provide selective flow of the gas. In the element 50, it is desirable to control the flow of the gas. To this end, a cellular element 53 (e.g., a porous channel element, a honeycomb member, or the like) is positioned in the housing 47 to cause the air or other gas to flow relatively evenly across the absorption sheet 44 rather than simply in certain areas. As shown, the air distribution manifold further includes an air inlet 51 and outlets 52 (with or without one-way check valves). The element 50 further includes an administration sheet 44, a diffusion membrane 45, and a conduit 43 between the cellular element 53 and the administration sheet 44. The housing 47 with the cellular element 53 forms a chamber 48 that creates a path for airflow away from the sheet 44 through the element 53, through the chamber 48, and out of the element 47 via the outlets 52.

The airflow comes in from the inlet 51 at a volume, flow rate, and duration selected typically to dry (to a desired level or substantially completely) the sheet 44. The airflow spreads in the conduit 43 and on the back side of the administration sheet 44, then flows through the cellular element 53 and the outlet 52 to the outside of the element 50. The solvent delivered onto the administration sheet 44 with the drug formulation is carried away with the airflow. Once the residual solvent in the administration film 44 and the membrane 45 is removed, the administration sheet 44 and the membrane 45 are dried which stops drug delivery. In this manner, a pulse pattern for drug delivery is realized by programming the drug delivery time and duration, and the airflow time and duration. In other words, the delivery of a drug or active substance can better be controlled not only by the accurate providing of a drug formulation to the element 50 but also the rapid and controlled removal of the formulation by drying of the sheet or reservoir 44. The flow rate and duration of the gas such as air may vary to practice the invention and may be selected depending upon the particular solvent utilized.

Figure 9:
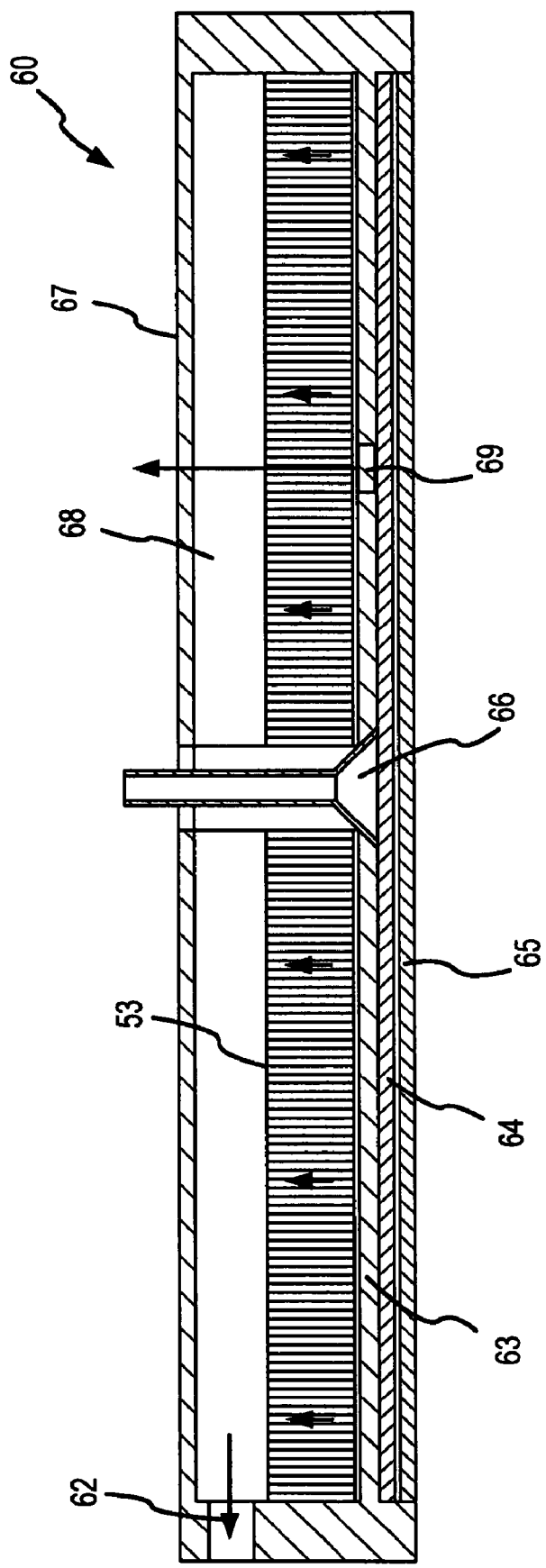
FIG. 9 is a cross-sectional view similar to that of FIGS. 6 and 8 showing another alternative embodiment of a delivery or administration element adapted for solvent removal and enhanced drug delivery by providing a heating or temperature control element proximate to the drug delivery membrane.

FIG. 9 shows a cross sectional view of an embodiment of an administration element 60 that can apply heat onto an administration sheet 64 to enhance drug permeation of the skin and to also enhance evaporation (as discussed above with reference to air/gas flow, which may be combined with heater element in some embodiments). The preferred embodiment 60 includes a housing 67, a tubing adapter with a conic end 66, a heat element 61, vents 62, an administration sheet 64, a diffusion membrane 65, a temperature sensor 69, and a conduit 63 between the heat element 61 and the administration sheet 64 (or reservoir). The housing 67 above the heat element 61 forms or defines a chamber 68 that creates a path for solvent evaporation. The heat element 61 can be turned on and off by programming and controlled by a microprocessor such as that provided in a typical control and display unit.

In some embodiments, a particular temperature is maintained at the administration area, such as 2 to 10 degrees Celsius and preferably at least about 4 degrees Celsius higher than typically body temperature when the device 1 is being operated for drug delivery as such a temperature range will significantly increase drug permeation or diffusion through the membrane 65 and into the skin. In some embodiments, the drug formulation is applied on the administration sheet 64 and the heat element 61 is turned on and left on or cycled during drug delivery operations or as needed to maintain a desired temperature or temperature range. The temperature sensor 69 is provided (e.g., embedded) in the conduit 63 and operates to sense the temperature on the administration sheet 64 and send a signal to microprocessor 91 through the interface 92. By this feedback control, the temperature on the administration sheet 64 can be kept at 4 degrees Celsius (or a range about this or another drug delivery set point) above the body temperature such as proximate to 40 degrees Celsius.

After drug delivery is completed, the heater element 61 may be operated to provide additional heat, such as by raising the temperature to 5 to 10 degrees Celsius or more above skin temperature, to hasten evaporation of the solvent from reservoir or absorbent sheet 64. Once the residual solvent in the administration film 44 and the membrane 45 evaporate, e.g., in about 30 minutes from experimental results, and the administration sheet 44 and the membrane 45 are dried, the heat element 61 is turned off (with this control being determined by a moisture sensor (not shown) or by experiential knowledge for a particular reservoir/sheet, solvent, heater, and temperature combination (e.g., a known operating time for drying based on results).

Figure 10:
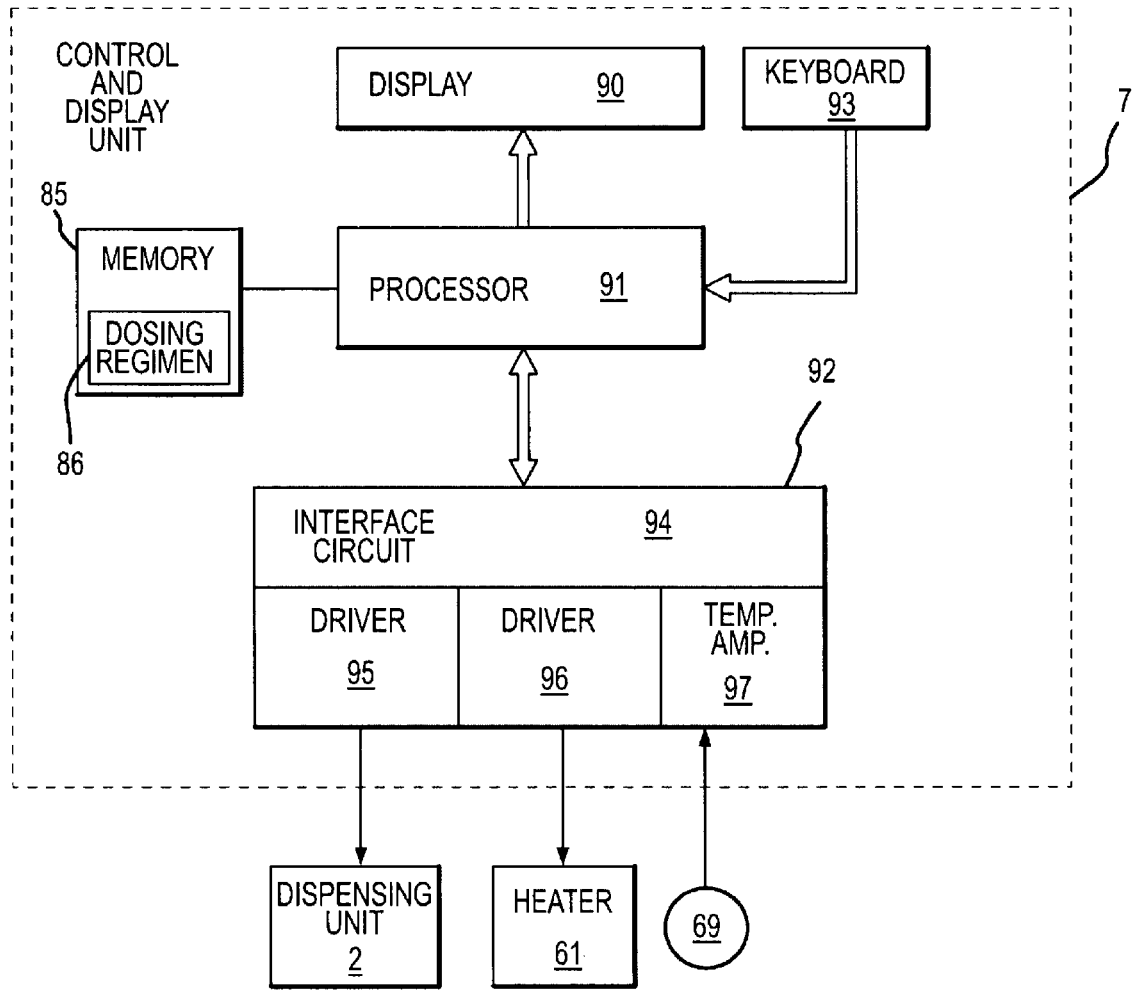
FIG. 10 is a block diagram showing components of a control and display unit for one embodiment of drug delivery device of the invention.

FIG. 10 shows an embodiment of the control and display unit 7 useful for realizing the functions of the one or all embodiments of this invention. The control and display unit 7 is one or several electric circuit boards with the microprocessor system 91, the display 90, the keyboard 93, and the interface 92. The unit 7 may further include one or memory devices 85 for storing dosing regimens or routines for running by processor 91 to control the operation (duration and speed to control flow rate) of the dispensing unit 2, the heater 61, and/or an air/gas source (not shown) to control diffusion rates for a device incorporating unit 7. The interface 92 includes an interface circuit 94, a drive circuit 95 for the dispensing unit 2 in the all embodiments; a drive circuit 96 for the heat element 61 and/or air/gas supply, and a temperature amplification circuit 97 for the temperature sensor(s) 69. The control signals and the measurement signals are output from or input to the microprocessor 91 through the interface circuit 94.

The dosing regimen 86 may be used to provide the flow rate for the pump/driving mechanism 2 and also the timing of its operation. A typical reservoir may provide drug volumes that can be applied for multiple days (such as for 3 or more days), and controlled transdermal release of an active material such as a drug can be timed and dosages selected to better match a body's rhythms to enhance chronopharmacological efficacy. Specifically, the co-pending and published U.S. patent application Ser. No. 11/162,525, entitled "Biosynchronous Transdermal Drug Delivery" filed Sep. 13, 2005, which is incorporated herein in its entirety by reference, describes the use of specific dosing regimens to select dosing (e.g., flow rates to the administration element) and also the timing of such dosages to enhance the effectiveness of the particular drug (e.g., treat heart attack and stroke in early morning hours, treat arthritis prior to a patient awakening, and the like). This references teaching is incorporated for use in configuring the dosing regiment 86 and otherwise for controlling operation of the processor 91 and other processors for operating the dispensing mechanism 2 (its flow rate and timing/duration of operation) and solvent removal components.

Figure 11:
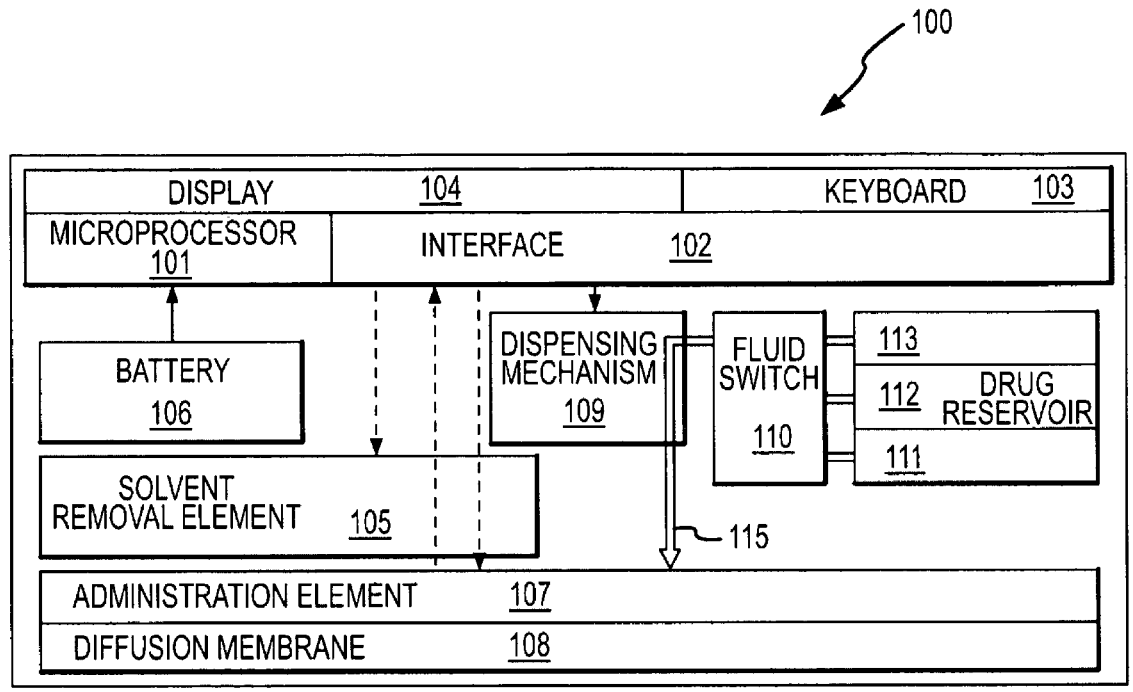
FIG. 11 is a block diagram similar to FIG. 2 showing another embodiment of a drug delivery system or device of the invention useful for multiple drug delivery.

Another embodiment of this invention of a device for transdermal drug delivery is shown in FIG. 11 as a device 100 for multiple drug formulations. The device 100 includes a control and display unit with a microprocessor system 101, an interface 102, a display 104, and a keyboard 103. Also, the device 100 includes a battery 106; a dispensing mechanism 109 (such as pumps 2 described above with an active and passive portion); drug reservoirs 111, 112, and 113; a 3-way fluidic switch 110; a solvent removal element 105; and an administration element 107 (such as a reservoir with a wicking filler or absorbent sheet) with a diffusion membrane 108.

The control and display unit may be similar as the unit 7 in device 1 of FIG. 1, except there is a control signal for the 3-way fluidic switch 110 to select one of the three drug formulations in the reservoir 111, 112, and 113 respectively. The fluidic switch is like a 3-way fluidic valve for 3-to-1 fluidic selection. Under the microprocessor 101 control, one of the three drug formulations can be selected to apply to the administration element 107 through the dispensing mechanism 109. In this embodiment, three drug formulations are presented but the number of the drug formulation can be 2 or 4 or more and is not limiting of the invention. The device 100 can be used to apply drugs or active substances sequentially with drying completed between dosing of each drug in reservoirs 111, 112, 113. Alternatively, two or more of the drugs may be applied to the membrane 108 via the administration element 107 and feed tube 115 by providing a volume of each liquid to the element 107 sequentially but with little or no gap between operation of mechanism 109 (e.g., apply drug in reservoir 111 and then immediately or after only a short delay the drug from reservoirs 112 and/or 113).

The dispensing mechanism 109 can be a peristaltic micropump (as discussed above) but can also be a diaphragm or other positive displacement micropump such as a piezoelectric micropump. The solvent removal element 105 can be a desiccant pack, a blowing-air element, or a heat element (or a combination thereof), as described in the other embodiments. The administration element 107 and the diffusion membrane 108 can be an absorption sheet laminated with a diffusion membrane. This embodiment shows dispensing multiple drug formulations separately and selectively by the control of the microprocessor 101, which is programmed according to a doctor's prescription.

Figure 12:
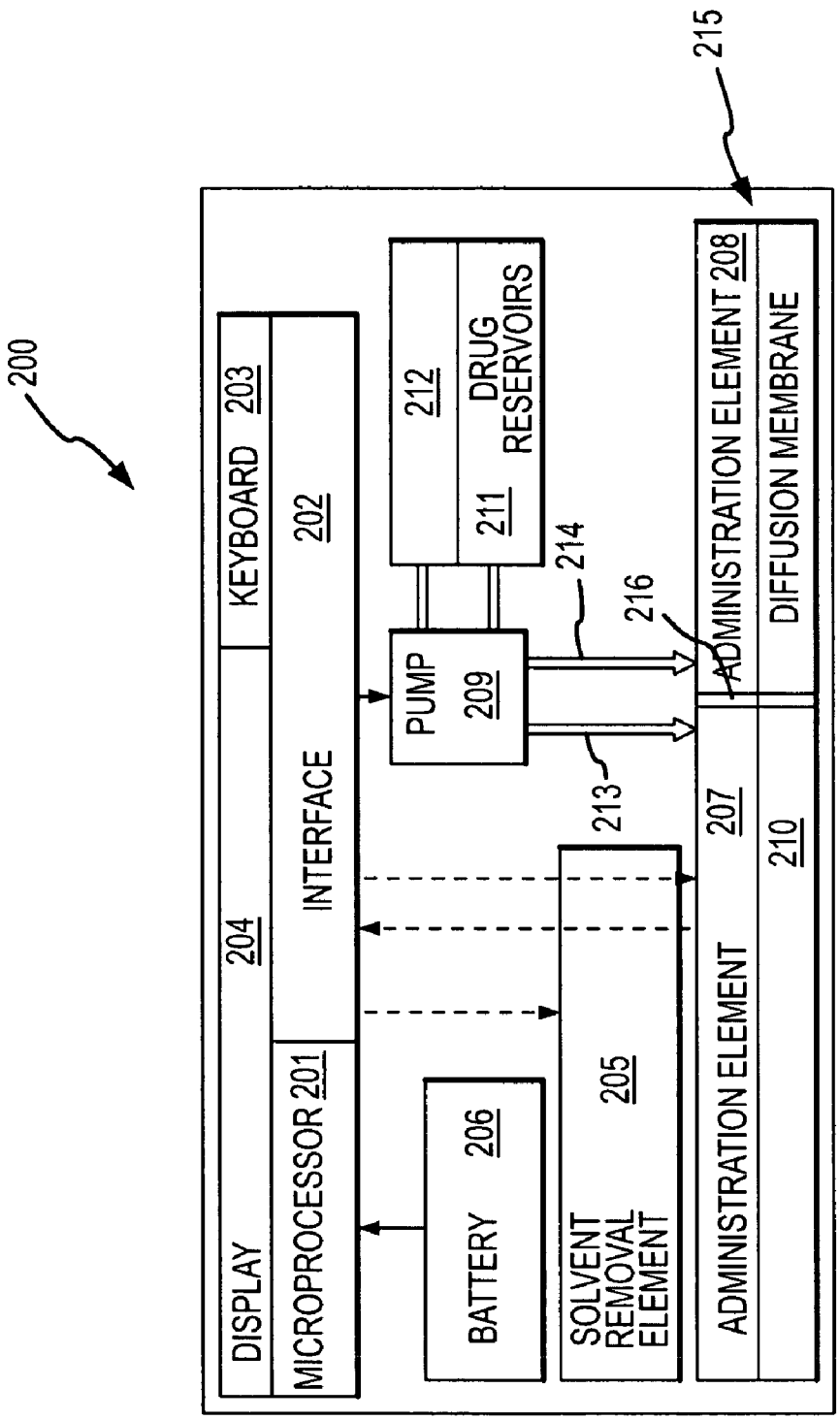
FIG. 12 is a block diagram similar to FIGS. 2 and 11 showing yet another embodiment of a drug deliver device of the invention that is useful for concurrent or sequential drug delivery.

Another preferred embodiment of this invention of a device for transdermal drug delivery is shown in FIG. 12 as a device 200 for concurrent delivery of multiple drug formulations (e.g., 2 or more). The device 200 includes a control and display unit with a microprocessor system 201, an interface 202, a display 204, and a keyboard 203. The device 200 further includes a battery 206; a dispensing mechanism or pump 209; drug reservoirs 211 and 212; a solvent removal element 205; and administration elements 207 and 208 with a diffusion membrane 210, which are separated into two areas by wall or separator 216. The device 200 is similar with the device 100 except that the device 200 can dispense multiple drug formulations simultaneously.

The dispensing mechanism 209 is a multiple channel liquid delivery device, such as a multiple channel peristaltic micropump. In this embodiment, two drug reservoirs 211 and 212 are connected to the dispensing mechanism 209, then under the control of the dispensing mechanism 209, applied to the administration elements 207 and 208 via feed tubes or channels 213 and 214. Even though the two drug formulations are demonstrated in this embodiment, the number of the drug formulations can vary and is not limited to two as shown in FIG. 12.

Figure 13:
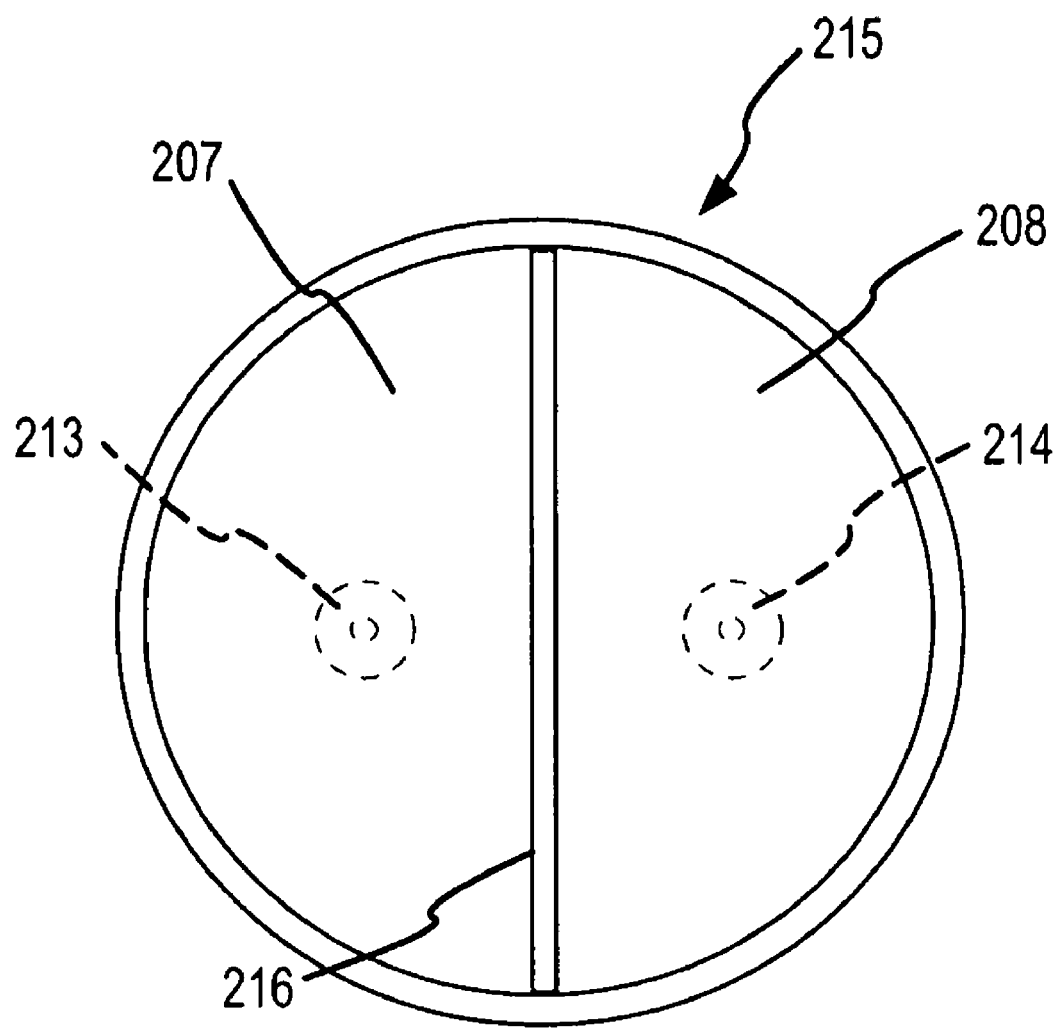
FIG. 13 is a simplified view of a drug delivery surface of a patch or membrane that is divided to provide separate delivery surfaces or areas as may be useful with the device of FIG. 12.

FIG. 13 shows an embodiment of the administration element 215 with the two administration areas 207 and 208 and a divider 216. The drug formulations are delivered to the conic ends of feed tubes or channels 213 and 214 by the dispensing mechanism 209. The diffusion membrane 210 is proximate to and in some cases in tight contact with the administration element 215 to provide an even diffusion of the drugs over its surface area. In this manner, two or more diffusion areas 207, 208 can be divided on the administration element 215 to provide multiple drug formulations delivery simultaneously.

While only transdermal drug delivery embodiments are shown, many of the features of the invention are equally applicable to subcutaneous drug delivery. For example, the inventors envision the use of the micropumps, such as the two part pumps and dosing capsules, to subcutaneous drug delivery in hospitals and other similar settings. In one such embodiment, the device 1 of FIGS. 2 to 10 and devices 100 and 200 of FIGS. 11 to 13 may be modified by replacing the administration element and membrane with a needle or coupling from the dispensing mechanism to an intravenous connection. In these embodiments, the pump may be the peristaltic pump which would allow the dosing capsule to readily be attached, detached, and replaced as described above to facilitate dosing with differing drugs without requiring disposable of the active portion of the pump and the display unit.

As discussed above, the dispensing mechanism of the invention may be a two-part (e.g., active and passive portions) peristaltic pump. Such a pump may take a number of forms to practice the invention, but the following discussion with reference to FIGS. 14-18 provides one useful embodiment of such a peristaltic micropump.

Various types of micropumps have been developed for delivering or dispensing a controlled flow of a liquid in a small, measurable (or known) quantity. In the field of drug delivery, it is recognized that supplying a drug in a correct temporal pattern is an important attribute of any drug delivery methodology. Controlled release drug delivery systems, such as those described herein, are intended to improve the response to a drug and/or lessen side effects of that drug. This is also important in the field of chronopharmacology, where biological rhythms are an important aspect of clinical pharmacology and are preferably taken into account when controlling a drug delivery system (or selecting a dosing regimen).

There has been an extensive amount of research into the design of various micropumps. Currently, most micropumps are driven by a piezoelectric element bonded to a flexible membrane covering the pump chamber. Many research groups have developed various micropumps such as pumps with pumping pressures over 7 m of water and micropumps using nozzles and/or diffuser components, which even at miniature length scales results in accurate flow volume control and high reliability. Some of these micropumps are relatively low cost, high performance silicon micropumps for disposable drug delivery systems (such as the micropump described in Maillefer, D., et al., "A High Performance Silicon Micropump for an Implantable Drug Delivery System," Technical Digest MEMS '99, pp. 541-546, 1999, which is incorporated herein by reference). Similarly, the piezoelectric diaphragm micropumps available from Star Micronics may be used in the dispensing mechanism of the invention, and generally include a diaphragm bonded to a piezo-ceramic element that mechanically vibrates to induce change of chamber volume and, thus, conveys fluid or gas through the pump chamber (which, in the embodiments described above, would be in the passive portion of the dispensing mechanism).

However, it should be noted that there may be some drawbacks to using piezoelectric materials to achieve a micropump (although they have been well developed where a pump element is oscillated by the application of electrical impulses on piezoelectric elements to create a pressure differential in a liquid). First, piezoelectric elements are formed from brittle crystal materials that are difficult and expensive to machine, particularly on small scales. Second, piezoelectric materials generally are not suitable for contacting liquids. Micropumps that exploit piezoelectric movement typically must be designed to insulate the piezoelectric material from contact with liquid. Third, even though the power consumption of the piezoelectric micropump is typically low, electrical circuitry with a high voltage supply is necessary to drive and control piezoelectric movement, which requires a certain voltage and current power supply to work. For portable devices and devices powered by a battery, this presents a challenge for using a piezoelectric pump in the dispensing mechanism.

In contrast, peristaltic pumps are desirable for use in the dispensing mechanism as they use a flexible tube that is compressed by a series of shoes on a roller to induce liquid flow. Such pumps provide a positive displacement and require little or no maintenance. A continuous tube that contains the fluid to be moved (such as in a cooling embodiment) or delivered sits between the shoes and a rigid wall (e.g., the curved surface provided the housing of the passive portion of the dispensing mechanism). The shoes pinch the tube against the wall as the roller is turned by an electric motor, which creates a positive pressure on the output side of the tube and a negative pressure on the input side. Peristaltic pumps are self-priming, and the only material in contact with the solution or liquid is the tube. Thus, a wide variety of fluid-compatible tube material can be selected to meet the life expectancy (e.g., the expected number of cycles and the like). There is a demand for a battery-driven or a low-voltage-driven micropump that is able to induce an amount of liquid flow. For life sciences, it is often preferable that the micropump be relatively inexpensive and disposable.

In general, the peristaltic micropumps of the invention include a motor, a housing, a housing cover, a roller with shoes, and a tube. The tube contains fluids and sits between the shoes on the roller and a rigid wall of the housing. The shoes pinch the tube against the wall as the roller is turned by an electric motor. Embodiments of the peristaltic micropump may include one or more of the following features. The roller or roller assembly may include a bracket upon which the shoes are mounted, e.g., with axes posts for the shoe mounting. The shoes on the roller may be an assembly of bearing or bushings that are mounted on the bracket of the roller. The minimum number of shoes are tow but typically three, four, or more are provided. The tube may be a module made from elastomer or rubber with a fluidic channel and fittings on the channel ends. The channels may be built such that the module can be pinched. The shape of the channel may be rectangular so that the channel can be easily pinched. Furthermore, the shape of the channel can be a specially designed shape that reduces the friction between the wall of the channel and the shoes on the roller and makes the channel fully closed by the compression of the shoes. Further, the housing cover may include a chamber that is built to accommodate a tube or tube module. On both the housing and the housing cover, alignment slots, bushings, and spring loaded tips may be provided to keep the tube module in the position where the shoes on the roller can pinch the channel in the module properly to cause liquid flow.

Figure 14:
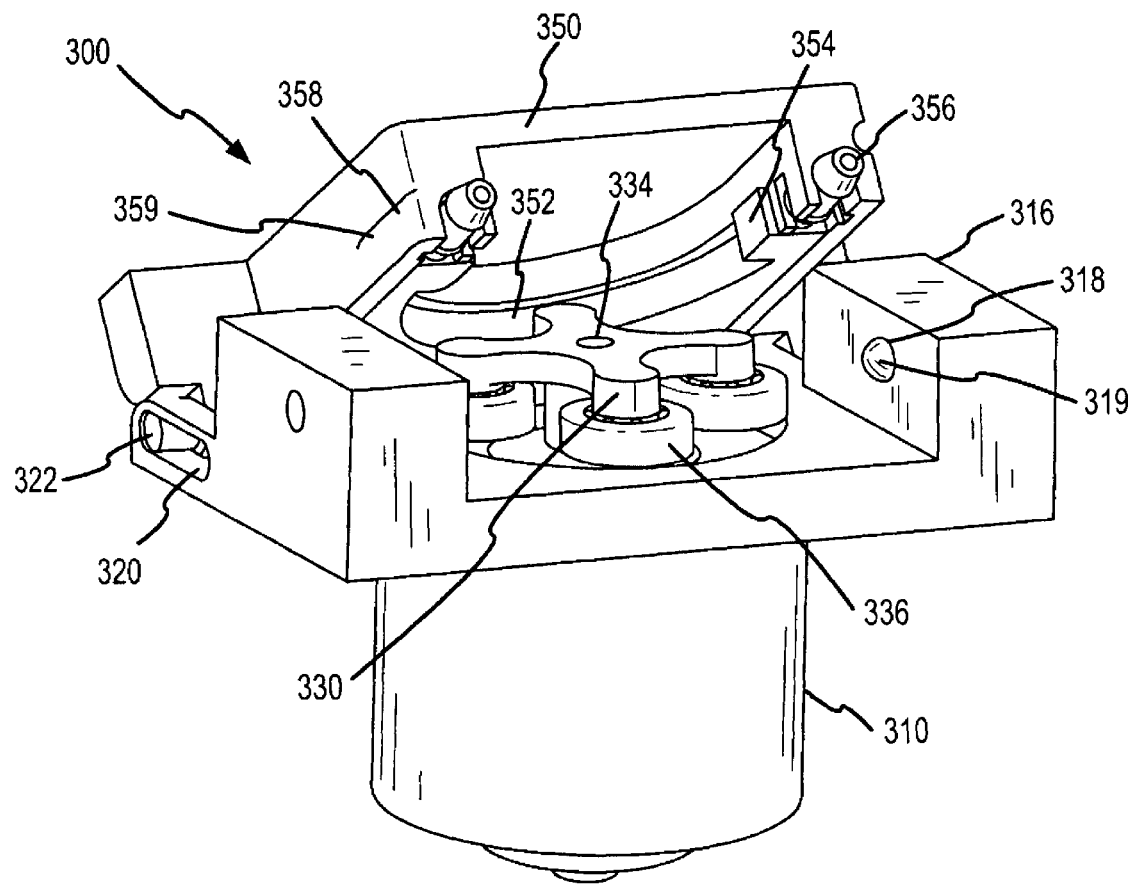
FIG. 14 is a perspective view of one embodiment of a peristaltic micropump of the invention, such as may be used as part of dispensing mechanism in the devices of FIGS. 1-13.
Figure 15:
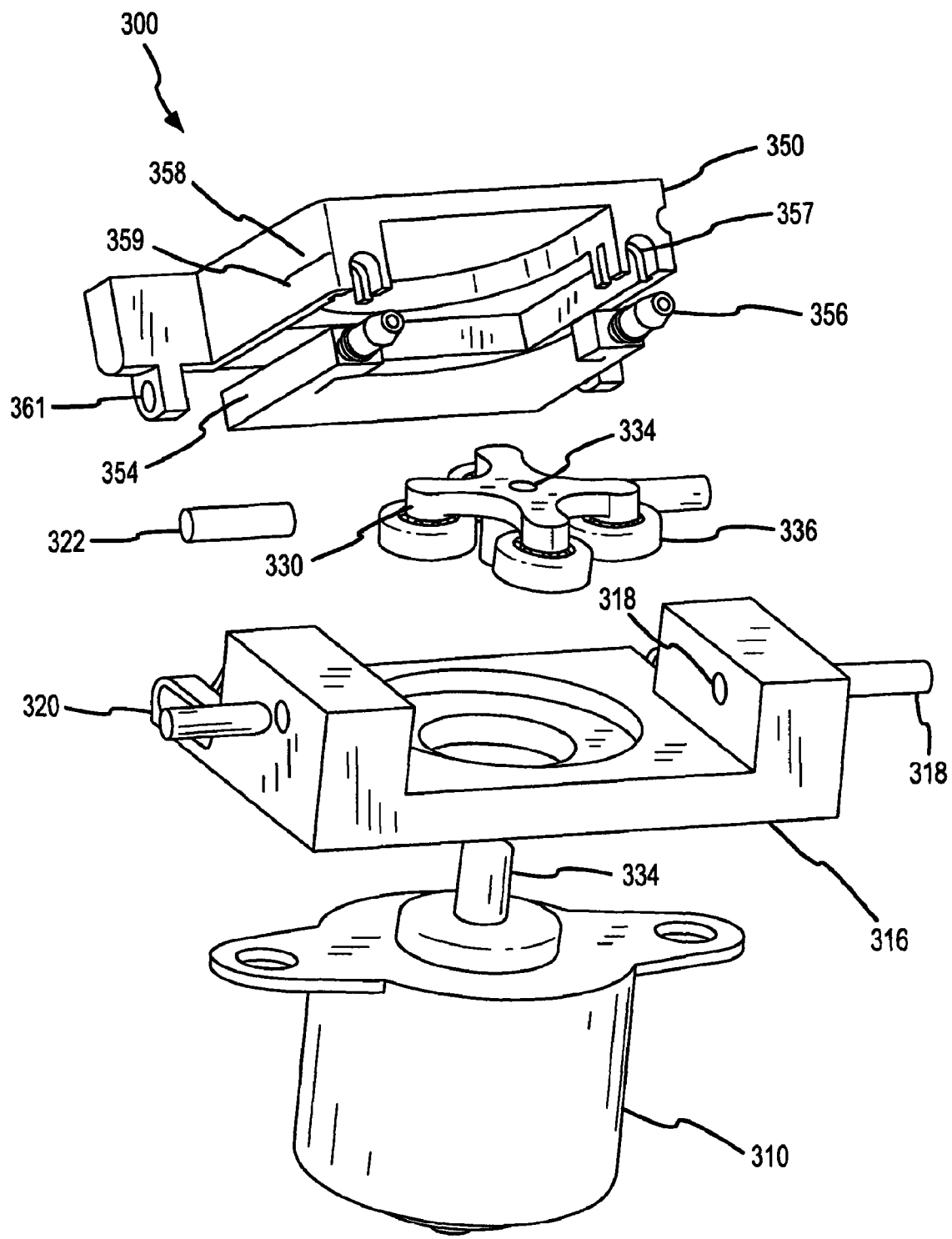
FIG. 15 is an exploded perspective view of the pump of FIG. 14.
Figure 16:
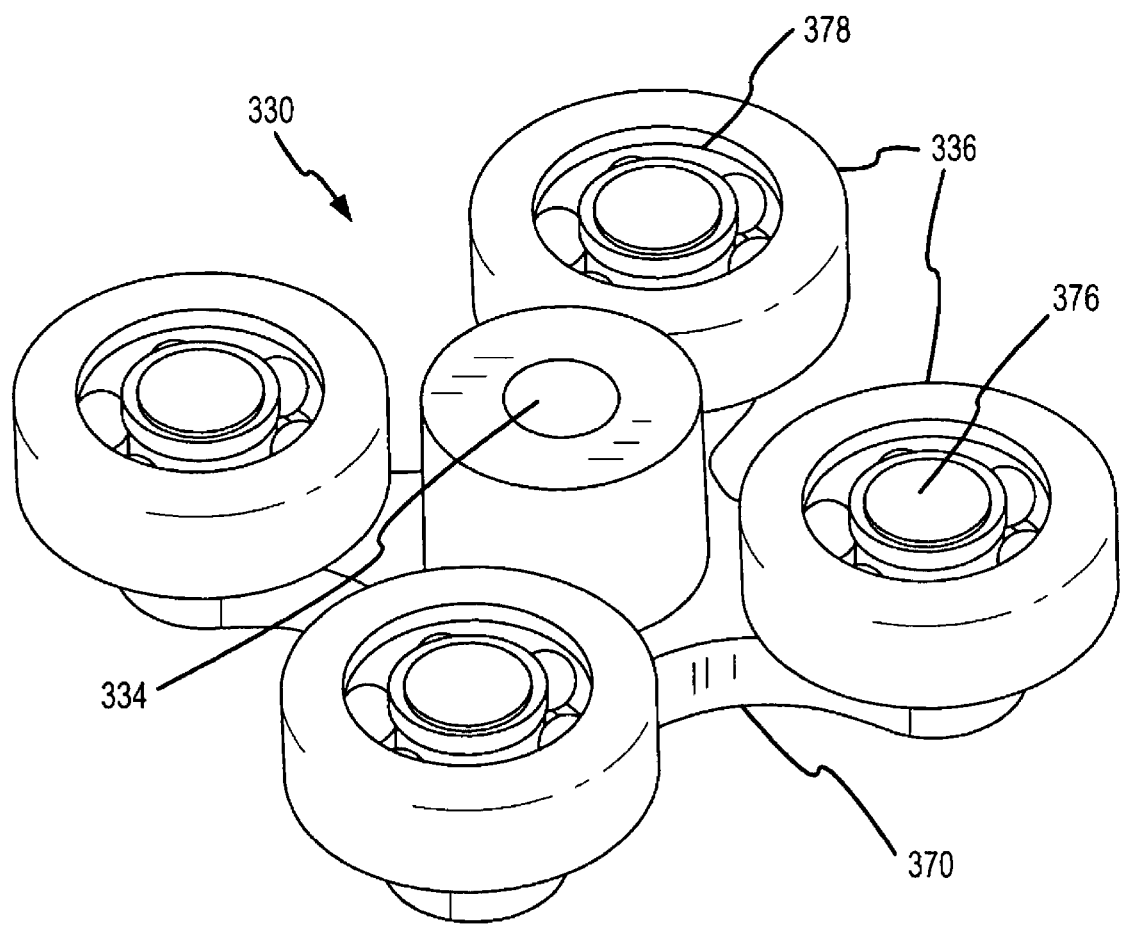
FIG. 16 is an enlarged view of the roller and shoe assembly of the motor shown in FIGS. 14 and 15.

FIGS. 14 and 15 illustrate a peristaltic micropump 300 according to one embodiment of the invention. This micropump 300 may be used for the dispensing mechanisms shown in the prior figures with the passive portion being the housing cover 350 and in some cases, the housing 316. As shown, the micropump 300 includes a motor 310 (e.g., an electric stepping motor that can be driven by a battery and controlled by the control and display units described above). The motor is attached to a housing 316 that mates with a housing cover 350. The housing 316 has sidewalls with holes 318 for receiving spring-loaded ball tips or other mechanisms for coupling with a housing cover 350. To achieve alignment, a slot 320 is provided in the housing sidewalls for receiving and allowing movement of alignment rods 322 of the housing cover 350.

Driven by the motor 310 is a roller 330 that mates with a drive shaft 334 of the motor 310. On the roller 330, a number of shoes 336 are mounted, e.g., 2 to 4 or more shoes about the periphery of the roller bracket, in a manner that allows each of the shoes 330 to spin about its central axis. During operation, the roller 330 spins about the central axis of the shaft 334, which is driven by motor 310 and the shoes 336 contact an outer tube surface and spin while applying compressive forces on the tube surface.

The micropump 300 is configured such that the active or driving portions (e.g., the roller and shoes) do not contact a liquid that is pumped. To this end, the micropump 300 includes a housing cover 350 with recessed surfaces for receiving a tube module 354. The tube module 354 functions to position a tube or feed/delivery chamber relative to the rotating or rotatable roller 330 and shoes 336 of the active portions of the pump. To this end, the module 354 includes tube fittings 356 that provide a coupling mechanism (such as a male tube fitting) for mating with a tube (not shown). The module 354 could be configured with a tube attached to the fittings 356 that places a tube in an arcuate or curved contact surface 352 in the housing cover (similar as the embodiments shown in FIGS. 2-13).

As shown, though, the module 354 is formed substantially as a single molded piece that has openings at the tube fittings 356 for receiving liquid such as from a tube attached to a drug reservoir (or a cooling reservoir or coolant source) at an inlet, for passing liquid through the internal cavity or chamber 353 (in FIGS. 17 and 18) of the module, and for passing liquid out the other fitting 356 to an outlet tube attached to the fitting (e.g., a tube connected to an administration element (or to a coolant loop or system). The outer surfaces of the module 354 are configured to abut the recessed surfaces 357 of the housing cover 350 and to also present a curved wall surface 352 for contacting the shoes 336 of the roller 330 when the roller 330 is rotated by the motor 310 via drive shaft 334. In this manner, the tube module 354 defines the feed or delivery chamber 353 for the solvent/drug mixture, coolant, or other liquid while also providing contact and positioning surfaces of the passive portion of a two-part peristaltic pump 300 rather than requiring a tube and a special configuration in the housing cover 350 to achieve tube alignment and to retain such a tube in a particular position or channel for contacting the shoes 336.

The motor 310 used to rotate the roller 330 can be either a DC motor or a stepping motor. On the housing 316 and the housing cover 350 there are alignment slots 320, 361 and rods 322 that keep both parts in position while the housing cover 350 is open or closed, such as when the tube of the tube module is changed or the tube module 354 is replaced. The housing cover 350 can be tilted up to 180 degrees for tube changing. On the housing 316 and the housing cover 350 there are also spring loaded ball keys 319 and key slots 358 and key holes 359 that keep the position for the tube module 354, such that the tube or module is pinched by the shoes 336 when the cover 350 is closed onto the housing 316 when the motor 310 is operated.

Figure 17:
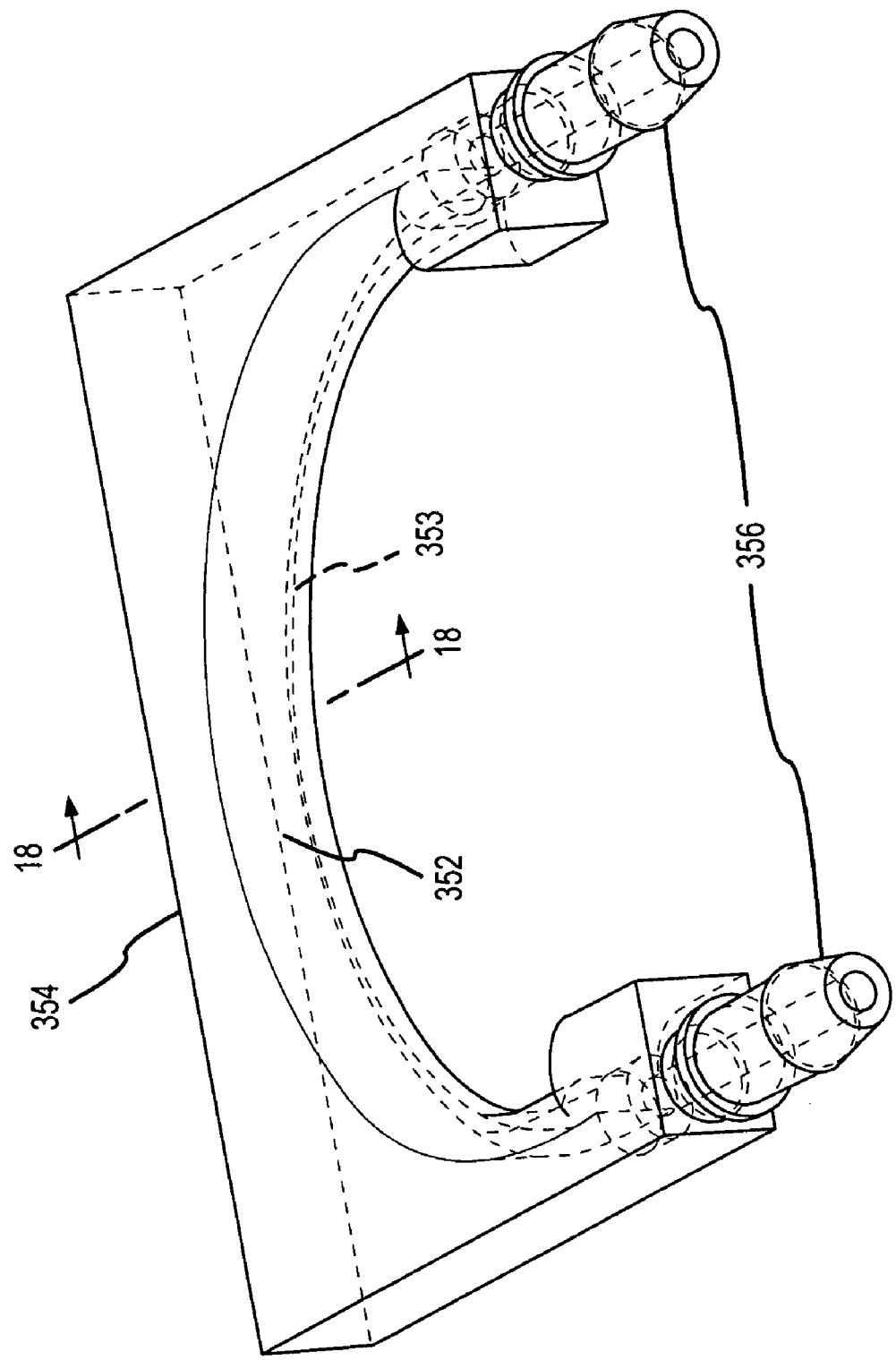
FIG. 17 is a detailed view of a tubing module showing the arcuate channel for receiving the tube and facilitating compression by the roller assembly.
Figure 18:
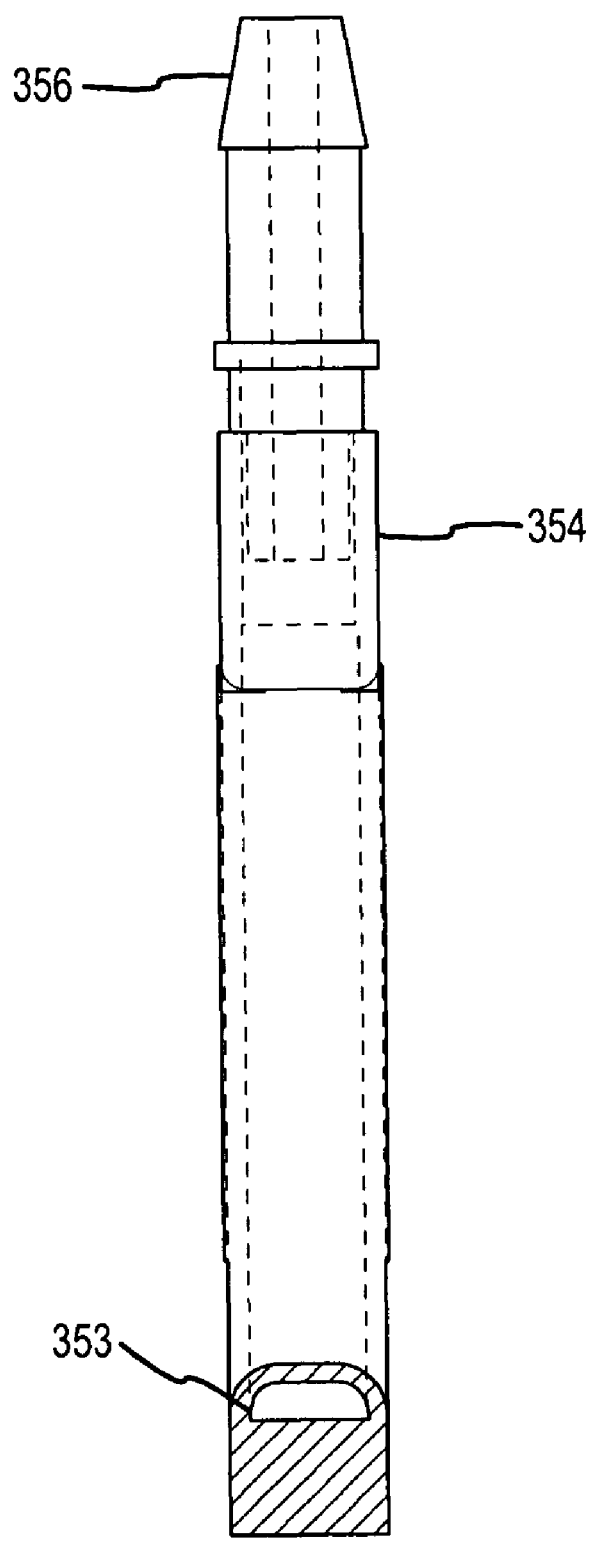
FIG. 18 is a cross sectional view of the tubing module of FIG. 17.

In the embodiment shown in FIG. 17, the module 354 may include the internal channel 353 and a curved wall 352 for receiving the shoes 336 on roller 330. This arrangement is further shown in FIG. 18, which shows tubing module 354 with a tube fitting 356 and a channel 353 for directing a known volume or flow of liquid through the module 354.

During operation, the roller 330 with the shoes 336 to pinch or apply compressive forces on the flexible tube is a key component as it is useful for obtaining a positive displacement and maintain an accurate flow in the tube module 354. The roller or roller assembly 330 is shown in more detail in FIG. 16, and, as shown, it includes a bracket 370 and the shoes 336, with a minimum number of shoes 336 being two with four being a useful number for many applications. On the bracket 370, there are provided bearing axis posts 376 upon which bearings 378 with shoes 336 are mounted. At the center of the bracket 370, a shaft sleeve is provided for receiving shaft 334, such as with a press fit or other mounting technique such that the sleeve and bracket rotate with the shaft 334. The shoes can be bearings or bushings, and in this embodiment 300, four bearings 378 for shoes 336 are mounted on the axis posts 376 on the bracket 370.

The pump tube is typically a consumable part and may be frequently changed to avoid any possible contamination. Given the small size of the micropump (e.g., several millimeters in its physical dimension and several micrometers to hundreds of micrometers on the tube dimension), changing such tubes may be difficult. Hence, the desirability either to provide a detachable, disposable passive portion as discussed with reference to FIGS. 1-13 or to providing a detachable and replaceable tube module 354 as shown in FIGS. 14-18. As shown, the "tube" or feed chamber is provided by the disposable module 354 with its channel 352 and its two tube fittings 356 for providing easy "tube" change outs while providing a desired, known flow rate accuracy. The tube module 354 is made in some cases from an elastomeric material that can be squeezed or compressed by the roller assembly 330 and its shoes 336.

The channel 353 may be a rectangular cross section channel built in or provided inside the tube module 354. The wall between the channel 353 and the contact surface 352 that is contacted by the shoes 336 is preferably thin enough so that the channel 353 can be squeezed or compressed to reduce its volume to create the desired pressures. The flat and rectangular-like shape of the channel 353 makes it easier to be squeezed. The dimensions of the channel 353 can be designed or selected to support a specific flow rates. On both ends of the tube module 354 there are provided two fittings 356 for quick fluidic connections with tubes (not shown) with the channel 353 (e.g., to connect the channel to a drug reservoir and with an administration element). In the housing cover 350, there is provided a chamber or recessed surface to accommodate or receive the tube module 354. The tube module 354 with the fittings 356 is plugged into the recessed surfaces 357 in the housing cover 350 as shown in the figures.

The peristaltic micropump 300 provides a number of advantages. The tube module of the micropump can be easily changed while the accuracy is retained. The bearings or the bushings (e.g., shoes) on the roller significantly reduce the friction between the shoes and the tube or tube module so that the heat generated from friction is decreased and the lifetime of the tube is extended. The channel in the tube module is, in some cases, rectangular in cross sections and this shape makes the channel more readily compressible (e.g., less compressive force is required). Therefore, the flow pressure is increased and the power consumption is decreased. The motor used to rotate the roller can be either a DC motor or a stepping motor. By simply applying variable DC voltage to the motor or sophisticatedly designing a stepping motor driver and a microcontroller, the micropump can be automatically controlled for its operation time and its flow rate (e.g., the micropump can readily be used to selectively deliver a specific volume of a drug/solvent mixture by controlling the timing of motor operation and its speed to deliver a specific flow rate through the micropump).

Figure 19:
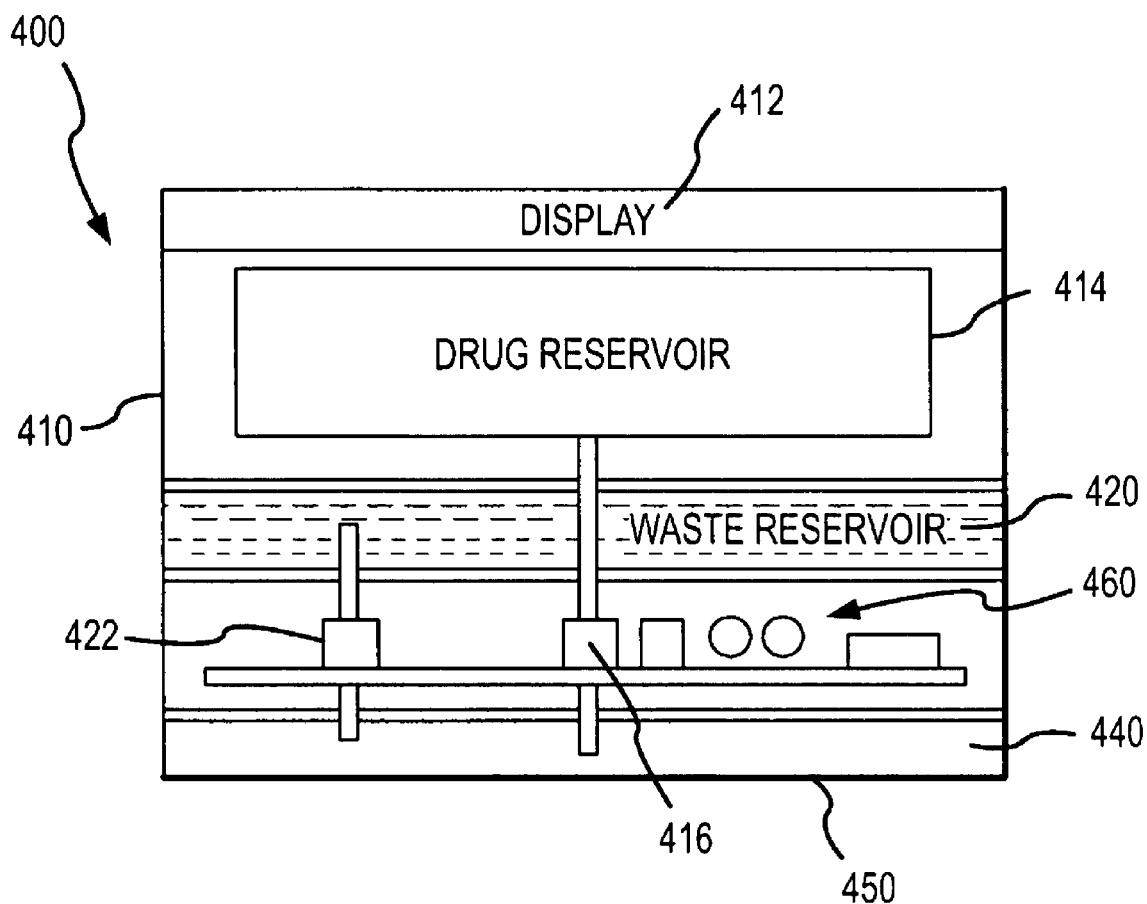
FIG. 19 is a sectional/block view of a delivery device with a waste reservoir for storing removed solvent/drug from an administration reservoir to control dosing.

FIG. 19 shows a cutaway, simplified block embodiment of an automated and programmable transdermal drug delivery device 400 that can stop dosing utilizing a flushing or removal means or assembly. As shown, the device 400 includes a housing 410, a display 412, a drug reservoir 414 for storing a liquid such as a drug formulation with a solvent and active substance, a micropump or other dispensing mechanism 416, control electronics 460, an administration reservoir 440, and a permeable membrane 450. Further included are a waste reservoir 420 for storing waste (e.g., liquid or drug formulation) removed by actuator or pump 422 that is in fluid communication with the reservoir 440.

In this embodiment, the administration reservoir 440 can be or include a substrate (not shown) including a plurality of micro-passageways for the drug formulation; a substrate formed of micro-structured and/or micro-fabricated reservoirs; a substrate including a series of miniaturized or micro-structured reservoirs, a substrate including a plurality of ducts, culverts and/or canals that may be any size, shape, or configuration, and which may be micro-fabricated through any number of techniques including etching. More specifically, in certain embodiments where the stoppage of permeation or dosing is desired, the active drug formulation or solvent initially is moved from the drug reservoir 414 to the administration reservoir 440 such as by controlled operation of the micropump 416 by electronics 460 (e.g., a controller operating to a dosing subroutine or the like). Then after the desired amount of time elapses to allow transdermal absorption (which may be programmed using the display 412), the mechanism to stop dosing, namely the second micropump or actuator 422 is activated by the electronic controller 460 to remove or flush the liquid or drug formulation and remaining volumes of the active drug from the administration reservoir 440 to the waste reservoir 420 to end permeation through the membrane 450 and adjacent skin.

In another embodiment not shown, the first micropump or actuator 416 accomplishes both the dosing into the administration reservoir 440 and the removal out of the administration reservoir 440 into the waste reservoir 420 after activation by the controller electronics 460 that responds to dosing instructions programmed into the display 412 by the user. In the embodiment appearing in FIG. 19, a second micro pump or actuator 422 accomplishes the removal or flushing of drug formulation out of the administration reservoir 440 into the waste reservoir 420 after activation by the controller electronics 460 that responds to dosing instructions programmed into the display 412 by the user in some embodiments or is based on a stored dosing regimen or profile in other cases.

The micropump or actuator 422 may be connected to an additional reservoir (not shown) containing water or an inactive solution, and this reservoir may be labeled or thought of as an inactive solvent reservoir (or flushing fluid source or reservoir). The second micropump 422 (or the first micropump 416 in some embodiments) then moves the inactive drug formulation (e.g., "flushing fluid" that may be selected for its inactive characteristics, to inactivate the active substance in the delivered drug formulation, or to otherwise better control/stop dosing) from the inactive solvent reservoir to the drug administration reservoir 440 to force out or flush the active drug formulation from the administration reservoir 440 into the waste reservoir 420 or into an area for evaporation (not shown).

In another embodiment, an air or gas cartridge can be utilized to force the active drug compound from the administration reservoir 440 into the waste reservoir 420 or into an area for evaporation pursuant to activation by the controller electronics 460 that responds to dosing instructions programmed into the display 412 by the user. It is important to note that when the administration reservoir 440, which acts as the administration depot for the transdermal absorption, is not an absorbent sheet or wick material but a micro-duct or culver or liquid passageway, it has at least one side, or a series of holes or openings (or otherwise) that allows the drug formulation to come into contact with the skin for transdermal absorption, either by passing through a membrane on skin 450 or otherwise to reach the skin for transdermal absorption. Such an administration reservoir 440 may take many forms to practice the invention such as a substrate comprising one or a plurality of micro-passageways for the drug formulation; a substrate of micro-structured and/or micro-fabricated reservoirs; a substrate including a series of miniaturized or micro-structured reservoirs, a substrate formed with a plurality of ducts, culverts, and/or canals that may be take any size, shape or configuration, and which may be micro-fabricated through any number of techniques including etching. This administration reservoir 440 in whatever form it may take may be filled using the micro-pump or actuator 416 to allow for the transdermal absorption, then flushed or emptied, as described above, so as to stop or slow drug delivery by removing the active drug from a position where it can access the skin for transdermal absorption.

As discussed above, a heating element may also be present (e.g., as shown in FIG. 9) whether directly formed in the substrate of the administration reservoir 440, provided as a separate component of the administration reservoir 440 either at the top, bottom, or side of the reservoir. This heating element serves to increase the temperature of the skin surface which increases the permeation of the active compound through the skin. This heating element aids in the movement of liquids through the passageways that may be provided in the administration reservoir 440. The heating element may also aid in the evaporation of the drug formulation where evaporation is a desired method to dry the administration area 440 to stop dosing by causing evaporation. This heating element may be programmed to automatically heat the skin at precise preprogrammed times for precise timing of permeation enhancement and/or precise timing of stopping of dosing by inducing evaporation. The heating element may be configured with a plurality of flow paths for vapor or evaporated portions of the liquid (such as solvent vapor) that facilitates relatively uniform or at least well distributed flow away from the reservoir.

A further embodiment that facilitates the stopping of dosing does not use the first, or introduce a second, micro pump or actuator to flush or empty the drug formulation from the administration reservoir 440. Instead, evaporation of the drug formulation or more specifically, the solvent, is induced so as to dry the administration reservoir 440 which will result in the stopping of dosing. It is well known that a dry skin/administration reservoir interface is not conducive to transdermal permeation. In this embodiment, the administration reservoir has vents or other access either to the environment for evaporation, or immediate access by being in close proximity to chamber containing a desiccant. This desiccant chamber acts to induce evaporation and captures the solvent vapors to dry the interface and stop dosing. In this embodiment, the heating element, which may be programmed via the display 412 or with stored software (e.g., a dosing profile) to heat at a certain time heats the administration reservoir 440 and/or skin and/or the whole device 400 which increases significantly evaporation and speeds up the process which in turn stops dosing quickly. As an alternative to heat, a gas or air cartridge can be present to automatically, pursuant to a programmed schedule programmed into the display 412, blow air or gas onto the administration area to rapidly dry the administration reservoir 440 and stop dosing.

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed. For example, the devices may also include components other than heating elements to enhance drug diffusion such as components to implement iontophoresis, sonophoresis, and/or mechanical or chemical permeation enhancers.

We claim:

1. An apparatus for transdermally delivering a drug formulation and stopping dosing or delivery in an automatic, controllable manner, comprising:
   (a) an active assembly comprising a controller;
   (b) a passive assembly adapted for mechanically coupling and decoupling with the active assembly, the passive assembly comprising:
      (i) a dispensing reservoir containing the drug formulation; and
      (ii) a delivery element comprising an administration reservoir and a membrane in fluid communication with the administration reservoir, the membrane being permeable to an active substance in the drug formulation;
   (c) a dispensing mechanism comprising:
      (i) an active portion in the active assembly providing a motive force to draw the drug formulation from the dispensing reservoir to the administration reservoir; and
      (ii) a passive portion in the passive assembly proximate to the active portion and defining a feed chamber through which the drug formulation flows from the dispensing reservoir; and
   (d) a stopping means for stopping dosing or slowing delivery by removing the drug or a solvent of the drug in the drug formulation from the administration reservoir, wherein the stopping means utilizes gas, air, fluid, or a combination thereof, which functions to flush the solvent, drug, or a combination thereof from the administration reservoir, and wherein the stopping means does not require removal of the apparatus from an application site during the flushing process.

2. The apparatus of claim 1, wherein the stopping means comprises a dispensing mechanism and a source of flushing air, gas, fluid or a combination thereof, the dispensing mechanism being selectively operable by the controller to pump the flushing air, gas, fluid or a combination thereof through the administration reservoir to a waste reservoir or evaporation element.

3. The apparatus of claim 1, wherein the stopping means comprises a micropump and a source of flushing air, gas, fluid or a combination thereof, the micropump being operable by the controller to pump the flushing air, gas, fluid or a combination thereof through the administration reservoir to a waste reservoir or evaporation element.

4. The apparatus of claim 1, the active assembly further comprising memory storing a dosing profile, wherein the controller operates the dispensing mechanism and the stopping means based on the dosing profile to initiate delivery of the drug formulation and to stop the delivery.

5. The apparatus of claim 1, wherein the stopping means utilizes gas, air, or a combination thereof, which functions to flush the solvent, drug, or a combination thereof from the administration reservoir.

6. A transdermal drug delivery device, comprising:
   (a) means for storing a first liquid and a second liquid each comprising a solvent and active substance mixture;
   (b) a pump comprising an active portion including a motor and a passive portion including a pair of feed channels connected to the storing means and a pump housing for detachably receiving the active portion;
   (c) an administration assembly comprising a reservoir connected to the feed channels for receiving the first and second liquids when pumped from the storing means by the pump and a membrane permeable to the active substances in fluid communication with the administration reservoir; and
   (d) a stopping means for stopping dosing or slowing delivery by removing the active substance or the solvent from the administration reservoir, wherein the stopping means utilizes gas, air, fluid, or a combination thereof, which functions to flush the solvent, drug, or a combination thereof from the administration reservoir, and wherein the stopping means does not require removal of the apparatus from an application site during the flushing process.

7. The device of claim 6, wherein the first and second liquids are pumped concurrently to the administration reservoir.

8. The device of claim 6, wherein the first and second liquids are pumped separately to the administration reservoir and the device further comprises a switch for selectively blocking flow through one of the feed channels.

9. The device of claim 6, further comprising a controller operating automatically based on a dosing profile to control operations of the pump.

10. The device of claim 6, wherein the stopping means utilizes gas, air, or a combination thereof, which functions to flush the solvent, drug, or a combination thereof from the administration reservoir.

* * * * *